(12) United States Patent
Barron et al.

(10) Patent No.: US 7,284,396 B2
(45) Date of Patent: Oct. 23, 2007

(54) METHOD AND SYSTEM FOR LASER MARKING IN THE VOLUME OF GEMSTONES SUCH AS DIAMONDS

(75) Inventors: Wes Barron, Kamloops (CA); Bruno Bourliaguet, Quebec (CA); Marc Levesque, St-Augustin-de-Desmaures (CA); Alain Cournoyer, Quebec (CA); Daniel Cantin, Sainte-Foy (CA); Yves Champagne, Sainte-Foy (CA)

(73) Assignee: International Gemstone Registry Inc., Kelowna (CA)

( * ) Notice: Subject to any disclaimer, the term of this patent is extended or adjusted under 35 U.S.C. 154(b) by 0 days.

(21) Appl. No.: 11/161,917

(22) Filed: Aug. 22, 2005

(65) Prior Publication Data

US 2006/0196858 A1    Sep. 7, 2006

Related U.S. Application Data

(60) Provisional application No. 60/656,915, filed on Mar. 1, 2005.

(51) Int. Cl.
*A44C 17/00* (2006.01)
*B23K 26/40* (2006.01)
*B23K 26/03* (2006.01)

(52) U.S. Cl. .............. 63/32; 219/121.62; 219/121.68; 219/121.69

(58) Field of Classification Search ........... 219/121.68, 219/121.69, 121.62, 121.83; 63/32
See application file for complete search history.

(56) References Cited

U.S. PATENT DOCUMENTS 4,392,476 A    7/1983  Gresser et al.

(Continued)

FOREIGN PATENT DOCUMENTS

JP    4-66283 A  *  3/1992

(Continued)

OTHER PUBLICATIONS

U.S. Appl. No. 10/607,184, filed Jan. 15, 2004, Patton et al.

(Continued)

*Primary Examiner*—Geoffrey S. Evans
(74) *Attorney, Agent, or Firm*—Paul Smith Intellecutal Property Law; Paul R. Smith

(57) ABSTRACT

A method and an apparatus for laser marking indicia in the volume of gemstones such as diamonds, the indicia being made up of a plurality of microscopic dot-shaped marks whose build-up can be initiated by exposing naturally-occurring internal defects or impurities in the volume of a gemstone to a tightly focused train of laser pulses. Authentication data is encoded in the gemstone from the relative spatial arrangement of the dot-shaped marks that form the indicium. Taking advantage of the presence of otherwise invisible defects in the gemstone allows for inscribing indicia with laser pulses carrying energies substantially lower than the threshold energy required for inscribing in the volume of a perfect gemstone material. The marking process is then much less susceptible to inflict damages to the surface of the gemstone, and the marking can be performed using a broad variety of femtosecond laser systems. The dot-shaped marks engraved at a depth below the surface of a gemstone can be made undetectable with the unaided eye or with a loupe by limiting their individual size to a few micrometres, while devising indicia made up of only a few marks. As a result, the marking does not detract from the appearance and value of the gemstone. The procedure for laser marking accounts for the random spatial distribution of the defects present in natural gemstones as well as for their strongly localized character. The presence of an indicium can be detected by using a dedicated optical reader that can be afforded by every jewellery store.

37 Claims, 11 Drawing Sheets

U.S. PATENT DOCUMENTS

| | | | |
|---|---|---|---|
| 4,467,172 A | 8/1984 | Ehrenwald et al. | |
| 5,149,938 A | 9/1992 | Winston et al. | |
| 5,206,496 A | 4/1993 | Clement et al. | |
| 5,410,125 A | 4/1995 | Winston et al. | |
| 5,521,984 A * | 5/1996 | Denenberg et al. | 382/209 |
| 5,573,684 A | 11/1996 | Winston et al. | |
| 5,656,186 A * | 8/1997 | Mourou et al. | 219/121.69 |
| 5,698,120 A * | 12/1997 | Kurosawa et al. | 219/121.83 |
| 5,753,887 A | 5/1998 | Rosenwasser et al. | |
| 5,761,111 A | 6/1998 | Glezer | |
| 5,828,405 A * | 10/1998 | Vanier et al. | 348/61 |
| 5,932,119 A | 8/1999 | Kaplan et al. | |
| 6,031,202 A * | 2/2000 | Arakawa et al. | 219/121.68 |
| 6,187,213 B1 * | 2/2001 | Smith et al. | 216/65 |
| 6,211,484 B1 | 4/2001 | Kaplan et al. | |
| 6,420,705 B2 * | 7/2002 | Chou et al. | 250/330 |
| 6,476,351 B1 | 11/2002 | Kaplan et al. | |
| 6,483,073 B2 | 11/2002 | Benderly | |
| 6,489,589 B1 * | 12/2002 | Alexander | 219/121.69 |
| 6,593,543 B2 | 7/2003 | Benderly | |
| 6,624,385 B2 | 9/2003 | Patton et al. | |
| 6,633,419 B2 | 10/2003 | Hosono et al. | |
| 6,664,501 B1 * | 12/2003 | Troitski | 219/121.69 |
| 6,684,663 B2 | 2/2004 | Kaplan et al. | |
| 6,713,715 B2 | 3/2004 | Christensen et al. | |
| 6,747,242 B2 | 6/2004 | Benderly | |
| 6,788,714 B2 | 9/2004 | Benderly | |
| 2001/0012055 A1 * | 8/2001 | Mori | 348/61 |
| 2001/0032831 A1 * | 10/2001 | Benderly | 219/121.68 |

FOREIGN PATENT DOCUMENTS

| | | | |
|---|---|---|---|
| JP | 9-182985 A * | 7/1997 | |
| JP | 2002-86282 A * | 3/2002 | |
| JP | 2004-223553 A * | 8/2004 | |
| WO | WO-00/32349 A * | 6/2000 | |

OTHER PUBLICATIONS

U.S. Appl. No. 10/607,185, filed Jan. 1, 2004, Patton et al.

J.B. Aschom, The Role of Focusing in the Interaction of Femtosecond Laser Pulses with Transparent Materials, Chpt. 4, Ph.D. Thesis, Harvard University, Cambridge, MA, Jan. 2003.

* cited by examiner

METHOD AND SYSTEM FOR LASER MARKING IN THE VOLUME OF GEMSTONES SUCH AS DIAMONDS

FIELD OF THE INVENTION

This invention generally relates to a method and system for laser marking of gemstones, and more particularly to a method and system for engraving authentication codes made up of a plurality of microscopic dot-shaped marks created by exposing localized internal defects present in the volume of a gemstone to a controlled train of laser pulses.

BACKGROUND OF THE INVENTION

The Marking of Gemstones

The previous inscription of a uniquely-defined identifying mark, or indicium, on a gemstone that has been stolen, lost, or mixed in a lot greatly facilitates its identification in case of recovery and its subsequent return to the rightful owner. As a result, insurance companies strongly encourage the marking of high-valued precious gemstones since most of these articles are insured. Likewise, inscribing an indicium that simply indicates the mining site or the country of origin of gemstones such as diamonds would be an efficient way to prevent from the entry of the so-called "conflict diamonds" in the legitimate diamond industry.

The marking of articles of various natures for purposes such as their unambiguous identification, classification, tracking, or ease of recovery is firmly established. The marked indicia can take the form of human-readable codes such as logos, artistic images, hallmarks, or serial numbers made from a stream of alphanumeric characters. Machine-readable codes such as the common 1-D bar codes or 2-D arrays of dot-like marks designed in accordance with various types of symbologies can be inscribed as well. Several distinguishing features of gemstones make their marking notoriously challenging. For example, indicia must be engraved on the surface of very small articles that generally comprise a large number of even smaller facets oriented in various directions. In addition, only a limited portion of the outer surface of a gemstone is accessible to marking when the stone is mounted in a setting. Adding to these difficulties is the fact that gemstones like diamonds are made from a material of extreme hardness while being subject to fracture upon sudden mechanical stress or excessive local heating. More importantly, inscribing a permanent indicium on a cut and polished gemstone must not impair its appearance, quality, and monetary value in any way.

Laser Marking of Indicia on the Surface of Gemstones

Among the various techniques that have been developed for the permanent marking of gemstones, laser marking has been known for a long time in the gemstone industry. A preferred method for laser marking relies on the use of a laser beam with suitable characteristics, the beam being directed on a polished surface portion of a gemstone. Some key characteristics of the beam such as the average power or energy per pulse, the focusing conditions, the wavelength and the duration of the laser exposure are chosen so as to ablate a shallow layer of the surface material. Various types of laser systems have been proposed and used for laser marking of gemstones. For example, U.S. Pat. Nos. 5,149,938, 5,410,125, and 5,573,684 all to Winston et al., U.S. Pat. No. 6,187,213 to Smith, U.S. Pat. Nos. 6,483,073, 6,593,543, 6,747,242, and 6,788,714 all to Benderly disclose the use of excimer lasers capable of delivering ultraviolet laser radiation, i.e., laser radiation having a wavelength shorter than about 400 nm (nm: nanometre, 1 nm=$10^{-9}$ m). Laser beams of shorter wavelength are preferred because the diameter of the engraved spots and the width of the engraved line segments scale with the wavelength of the beam. Note that most natural diamonds are of type Ia. Their ultraviolet absorption edge occurs at a wavelength of about 291 nm, so that they are substantially transparent for wavelengths in the visible region, which spans from 400 nm to about 700 nm. Nevertheless, solid-state laser systems have also been found attractive as laser sources for marking gemstones, particularly when their primary output beam is frequency doubled to get a final output wavelength typically in the range of 500 nm to 600 nm in the visible region. The use of Nd:YAG laser sources for engraving at the surface of gemstones has been disclosed in U.S. Pat. No. 4,392,476 to Gresser et al., U.S. Pat. No. 4,467,172 to Ehrenwald et al., U.S. Pat. No. 5,753,887 to Rosenwasser et al., and U.S. Pat. No. 6,713,715 to Christensen et al., while the use of Nd:YLF lasers has been taught in U.S. Pat. Nos. 5,932,119, 6,211,484, 6,476,351, and 6,684,663 all to Kaplan et al. Laser beams having a sizeable cross-sectional area when hitting the surface of the workpiece can produce ablated patterns with complex shapes through the use of a mask in which are machined cut-outs that precisely reproduce the shape of the desired pattern. Alternatively, indicia having complex patterns can be etched with a laser beam tightly focused to a very small spot at the surface of the workpiece. In this purpose, the workpiece can be mounted on a motorized XYZ translation stage with pre-programmed displacements. Another approach consists in using a beam steering apparatus to scan in a controlled manner the laser beam over a limited surface area of a workpiece, which is held immobile. Even with a tight focusing, the average power or energy per pulse available from a laser source can be insufficient to reach the surface ablation threshold of precious gemstones such as diamonds, which are made up of a very hard and generally transparent material. In this case, a light-absorbing material such as a dye or ink coating can be deposited on the surface of the workpiece prior to exposure to the laser beam. An alternative to the deposition of light-absorbing coatings is the use of a pulsed laser source capable of emitting laser pulses of duration less than about 1 ns (ns: nanosecond, 1 ns=$10^{-9}$ s) to lower the threshold energy for vaporization of most materials, as taught in U.S. Pat. No. 6,713,715 to Christensen et al.

The indicia engraved using variations of the general technique as disclosed in the patents cited above do not impair either the appearance nor the grading of gemstones because the marks are generally engraved on a surface portion of the girdle of the gemstones. In particular, the marks engraved on diamonds often show some darkening due to the growth of a superficial layer of graphite during the laser ablation process. In many circumstances, the presence of graphite is of minor concern and, in fact, it may help to provide a better visibility of the indicia when they are intended to be read using a low magnification loupe. If desired, the layer of graphite can be removed with a surface treatment. An example of such a treatment is recited in U.S. Pat. No. 4,467,172 to Ehrenwald et al, and it consists in the application of 700° C. of heat combined to hydrochloric acid. Besides the highly contrasting appearance of the indicia caused by the presence of a layer of graphite in the etched surface areas, any indicium can be made more easy to detect and to recognize simply by enlarging it. An advantage of inscribing easily visible indicia having sizeable dimensions is that they may act as efficient theft deterrents in some particular situations.

Unfortunately, visible indicia inscribed directly on the surface of gemstones can be easily counterfeit by a simple repolishing of the engraved surface portion of the girdle or by using other types of surface treatments, this operation being possibly followed by the marking of a new but illicit indicium. A surface treatment aimed at defeating an indicium engraved on the surface of a gemstone would consist for example in removing any trace of graphite in the etched pattern, if any, and then to fill in the etched regions with a kind of fracture-filling product well known in the art. Even though the marking on a surface portion of the girdle does not detract from the appearance and grading of a gemstone, an indicium inscribed on the girdle may become hidden if the marking is carried out on a loose gemstone, prior to mounting it in a setting. Many settings have grips that prevent from getting visual access to the entire surface of the girdle.

In some other circumstances, however, it can be desired that the identification marking be as covert as possible to prevent unauthorized detection. An obvious way to reach this goal is to inscribe indicia of very small overall dimensions. As mentioned previously, the size of the smallest features that can be inscribed with a laser beam focused with conventional optics is fundamentally limited by the wavelength of the light, reaching what it is called the optical diffraction limit. Unfortunately, powerful, reliable and affordable laser sources emitting at wavelengths shorter than about 190 nm and configured for use in industrial environments are still lacking.

A major advance in the existing methods for laser marking at the surface of gemstones has been realized by using a special technique known as near-field optics. U.S. Pat. No. 6,624,385, U.S. application Ser. No. 10/607,184 and U.S. application Ser. No. 10/607,185 all to Patton et al. disclose the use of near-field optics for the marking of gemstones with a variety of laser sources such as excimer lasers and frequency-doubled Nd:YAG lasers. This technique enables the inscription of "micro-indicia" made up of features having dimensions well below what is allowed by the optical diffraction limit. Near-field optics can be implemented by delivering the laser light through tapered optical fibers or, more preferably, through the use of a solid immersion lens whose flat output surface is set in close contact with a surface portion of a gemstone.

In addition to the known shortcomings of the laser marking on the surface of gemstones, marking micro-indicia of very small dimensions can make them difficult to locate in a reasonable time delay. Generally, a search key must be provided or the micro-indicia must be inscribed at precise locations relative to some obvious landmarks on the stone, such as the geometric centre of the table. In addition, the reading of subtle micro-indicia is generally performed through the use of complex and expensive devices. Finally, a counterfeiter can easily repolish the whole outer surface of a stolen gemstone to eliminate traces of any imperceptible micro-indicium.

Laser Marking of Indicia in the Volume of Transparent Materials

Independently of its overall size and complexity, an indicium can be made very difficult if impossible to counterfeit by engraving it well below the surface of a gemstone while leaving the exterior surface unaltered by the marking process. The layer of material located between the indicium and the exterior surface then acts as a thick protective barrier, so that altering the indicium becomes very difficult without inflicting severe and irreversible damages to the article marked in this way. Methods for sub-surface marking with a laser beam have been developed to mark objects whose properties, dimensions, and uses differ radically from those of common gemstones. For example, U.S. Pat. No. 5,206,496 to Clement et al. discloses the sub-surface laser marking of areas of increased opacity in the body of transparent materials such as glasses and plastics. The technique has been proposed for the marking of containers that serve for example to contain expensive fragrances that are distributed to a limited number of authorized retail outlets. Marking in the volume of a material offers the advantage of not only being able to withstand any surface treatment (including repolishing) aimed at destroying the indicium, but also of being very difficult to replicate by counterfeiters. Laser marking below the surface of diamonds is briefly taught in U.S. Pat. No. 4,467,172 to Ehrenwald et al, but no details are provided about the control of the shape, dimensions, and depth of the sub-surface occluded marks.

The inscription of marks (also referred to as "microstructures") in the bulk of various transparent materials with a laser beam is a concept that offers great promise for the writing of two- and even three-dimensional arrays of densely packed point-like marks for permanent optical data storage applications. The concept is also attractive for building optical waveguides that serve to channel light in the bulk of optical materials such as fused silica. Both types of applications mentioned above call for the use of a write laser beam with tightly controlled temporal and spatial characteristics in order to inscribe microstructures of precise dimensions and shapes in the volume of a transparent material without inflicting any undesired optical damage to the bulk of the material or to its outer surface. While being primarily focused on optical information storage applications, U.S. Pat. No. 5,761,111 to Glezer discloses the use of ultrashort laser pulses to produce crack-free, regularly-shaped microstructures of high-contrast refractive index in a variety of transparent materials. These materials include fused silica, plastics, semiconductors, sapphire, and even fine crystals and jewelry. Three different marking regimes are discussed in the above-cited patent, the first one providing better control of the shape and dimensions of the inscribed microstructures. This regime relies on the use of a tightly focused pulsed laser beam with extremely short pulse duration, i.e., in the range of a few fs (fs: femtosecond, 1 fs=$10^{-15}$ s) to about 200 ps (ps: picosecond; 1 ps=$10^{-12}$ s). Another requirement of this specific marking regime relates to the energy carried by each laser pulse, which must be comparable or a few times higher than the threshold energy required to induce permanent structural changes (damages) in the host transparent material, for the selected laser wavelength and focusing characteristics.

Successful demonstration results of this sub-surface marking technique have been reported in the above-cited patent and in journal papers such as E. N. Glezer et al, "Three-dimensional optical storage inside transparent materials", Optics Letters, Vol. 21, pp. 2023-2025, (1996), and E. N. Glezer et al., "Ultrafast-laser driven micro-explosions in transparent materials", Applied Physics Letters, Vol. 71, pp. 882-884, (1997). For example, the authors succeeded in writing a two-dimensional array of low-contrast refractive index microstructures spaced from each other by about 2 μm (μm: micrometre, 1 μm=$10^{-6}$ m) and having diameters in the range of 200-250 nm when observed from the face on which the write laser beam was incident. The microstructures were written at a depth of 100 μm below the surface of a recording medium made of fused silica. However, the patent and the related journal papers cited above failed to report on any successful attempt at marking in the bulk of a diamond material. In fact, the above references merely mention that the energy threshold for inducing structural changes in the bulk of diamonds is higher than those of most other transparent materials by a factor of at least 100.

Laser Marking in the Volume of Diamonds

Intrigued by the inconclusive situation just described above, and presumably unaware of U.S. Pat. No. 4,467,172 to Ehrenwald et al., J. B. Ashcom undertook more systematic experimental studies aimed at marking in the bulk of natural Ia and IIa single-crystal diamond samples with femtosecond laser pulses. He reported on his main results in Chapt. 4 of the Ph.D. thesis entitled "The Role of Focusing in the Interaction of Femtosecond Laser Pulses with Transparent Materials" (Harvard University, Cambridge, Mass., January 2003). Ashcom observed that directing a train of femtosecond laser pulses on the same spot in a diamond sample may produce optical damage (microstructures) in the bulk of the sample, but only when focusing the laser pulses with a microscope objective having a numerical aperture in the range of about 0.25 to 0.45. Ashcom undoubtedly succeeded in marking microstructures at a depth of about 40 μm below the surface of a diamond sample, using laser pulses carrying an energy that was varied in the range from about 20 nJ (nanoJoules) to 90 nJ. Surprisingly, a salient feature of his experimental investigations is the observation that even at the highest energy level and for the greatest number of pulses he used, there were instances where no internal damage was produced in the natural diamond samples. Likewise, there was a significant statistical component to the onset of the laser-induced damage from site to site in the same diamond sample, as well as from sample to sample. Spatial variations in the concentration of impurities present in its natural diamond samples were postulated as the cause of such a stochastic behaviour. The Senior thesis of an another member of the same group (J. C. Hwang, Harvard University, Cambridge, Mass., April 2003) also reports that the created microstructures had a dark and opaque appearance, which was hypothetically attributed to the presence of graphite, and more likely to the formation of amorphous carbon inside of each microstructure. Being aware of such results, Ashcom concluded that the successful marking in the bulk of diamonds was unlikely.

The crucial role played by the impurities and defects in the creation of marks in the bulk of a gemstone material is more clearly evidenced from the photomicrograph shown in FIG. 1A. Five laser pulses of about 150-fs duration and carrying an energy per pulse of about 500 nJ were focused all in the same volume within a natural diamond sample. Instead of a single mark centered on the peak of the focused beam intensity profile, FIG. 1A shows that at least three distinct marks have been created, each of them being located out of the volume in which the write laser beam got its narrowest transverse spot size. The local optical fluence at the position of each dark spot visible in the figure was then significantly lower than the peak fluence of the write laser beam, but it was nevertheless sufficient to initiate structural changes at places where well-localized defects and impurities were present in the material. FIG. 1B presents a further evidence of the localized nature and random distribution of the naturally-occurring defects and impurities. The figure shows a photomicrograph taken over a surface area of a natural diamond sample over which a tightly-focused femtosecond laser beam was translated along a linear trajectory at a constant velocity of 1 mm/s. The laser pulses of 50 μJ of energy were delivered at a rate of 1 kHz, and the trace shown in the figure spreads over a length of about 2 mm. The photomicrograph shows that the trace inscribed in the bulk of this specific natural diamond sample is far from being continuous, since it is made up of small dark spots randomly distributed along the trajectory. A striking feature of the photomicrograph is the presence of a long segment of the trace, located in the center region of the figure, that is free from any dark spot. On the other hand, the dark spots appear densely packed in some regions of the left-hand portion of the trace. In addition, many of these spots are located either above or below the center line of the trajectory, meaning that they have been formed in sites where the local optical fluence of the beam was not at its maximum peak level.

From the results presented in FIGS. 1A and 1B, it can be concluded that an appropriate choice of the energy per pulse is important to the successful marking of microstructures in natural diamond samples. For instance, if the energy per pulse is excessive, as it was the case in the example shown in FIG. 1A, several off-centered marks can be formed around (and slightly above) the targeted volume in the material. On the other hand, shooting with laser pulses having insufficient energy can result in failure to mark in volumes where defects are presumably absent. It is then expected that the proper range of energy per pulse may vary from site to site in the same natural diamond sample to get rid of the localized nature and random distribution of the defects from which the creation of the microstructures is initiated. The energy per pulse also impacts heavily on the subsequent growth of the inscribed marks. For example, FIG. 5C shows a photomicrograph taken across a surface area of a natural diamond sample in which a set of marks have been inscribed with a train of five laser pulses. The energy per pulse was in the range of a few μJ, and it was varied from site to site. The marks visible in FIG. 5C as black areas with irregular contours were inscribed in a natural diamond sample that was previously cut to give it the shape of a cube. The cubic shape allows the visual observation of the marks from any flat side wall of the sample, thus giving precious information about the spread of the microstructures along a direction parallel to the propagation axis of the write laser beam. In FIG. 5C, the write laser beam was then incident on a surface of the sample located at the top of the figure, and it propagated parallel to the downward direction in the figure. In this specific example, the extent of the microstructures along the vertical direction reaches more than 100 μm at the highest energy level used in the tests, as shown for both marks located in the right-most portion of the figure. As a result, both marks appear as dark spots with a diameter of about 30 μm when observed from the surface of incidence of the sample.

It was found that once a structural change has been initiated from a defect or impurity in a diamond material, the subsequent growth of the mark can be controlled by a proper selection of the key parameters of the marking process, such as the energy per pulse, the number of laser pulses directed onto each site within the sample, and the focusing characteristics of the write laser beam. However, a combination of laser parameters that is found suitable for a specific site in a gemstone material does not necessarily hold for any other site in the same gemstone, thus preventing from the development of a universal laser marking protocol. In fact, any operative laser marking protocol must include a real-time monitoring of the growth of each individual mark in order to stop the laser marking once the mark has the desired overall dimensions. This aspect is important for the inscription of indicia that do not detract from the appearance and grading of the marked gemstones.

In view of the prior art recited above and of the various problems and challenges reported when implementing the related techniques for laser inscription of indicia on the surface or below the surface of gemstones, there is a need for a method and a system that would enable reliable, safe, and controlled marking of indicia in the bulk of gemstones such as diamonds. There is also a need for a system that can account for the stochastic nature and variations in the marking processes developed so far, along with the peculiar physical properties of the natural diamonds in the formation of laser-induced microstructures therein.

OBJECTS OF THE INVENTION

It is therefore a first object of the present invention to provide a method and an apparatus for laser inscribing permanent dot-shaped marks in the volume of gemstones such as diamonds, at some predetermined depth below the surface of the table, and without causing any laser-induced optical damage at the surface of said table, so that the inscribed marks are impossible to erase using any type of surface treatment while being very difficult for counterfeiters to imitate.

It is another object of the present invention to provide a method for laser marking in the volume of diamonds by taking advantage of the presence of defects and impurities randomly distributed within the crystal lattice of natural diamonds to trigger the controlled growth of dot-shaped marks by exposing diamonds to laser pulses with durations in the femtosecond range and carrying an energy per pulse well below the energy threshold for marking in the bulk of the otherwise perfect diamond material. It is still another object of the present invention to provide a method for safe marking in the bulk of diamond gemstones of the highest clarity, using a laser system that delivers laser pulses with an energy high enough to induce structural changes in the bulk of a perfect diamond crystal lattice.

It is another object of the present invention to provide a method and an apparatus for laser marking in the bulk of gemstones such as diamonds, and that offer sufficient versatility to enable the marking of gemstones with largely varying clarity and quality, having various cuts and overall sizes, and which can be either loose or mounted in various types of settings at the moment they are marked.

Yet another object of the present invention is to provide a method for laser inscription of dot-shaped marks in the volume of gemstones, each mark being small enough to remain undetectable when viewed with instruments of common use by diamond graders, in order not to detract from the appearance, grading and monetary value of the gemstone marked according to the method of the present invention. On the other hand, it is a further object of the invention to tailor the dimensions and shape of the marks in order to make them machine-detectable by a dedicated optical reading system.

Still another object of the present invention is to provide a procedure for marking indicia in a totally safe manner in the bulk of gemstones such as diamonds, the procedure being designed to properly account for the stochastic nature of the formation of laser-induced marks in the bulk of natural diamonds, which exhibit concentrations of defects and impurities that vary largely from site to site in their volume.

It is a further object of the present invention to provide a simple, low-cost, and easy to use optical reading system based on a conventional optical microscope design and capable of providing images of the dot-shaped marks inscribed in the bulk of a gemstone, these images having sufficient contrast to enable reliable and automatic detection of the overall indicium by an image processing means.

It is another object of the present invention to provide a method for encoding authentication data in the bulk of gemstones such as diamonds by laser inscribing a uniquely-defined indicium made up of a very few number of dot-shaped marks, the marks being well separated from each other so that the appearance, grading, and monetary value of the gemstones remain unchanged upon marking.

It is another object of the present invention to provide gemstones such as diamonds having a personnalized, self-authenticating indicium inscribed in their bulk and that preserves their initial quality and monetary value.

These and other objects of the invention will be more fully appreciated by reference to the summary of the invention and the description of the preferred embodiment that follows.

SUMMARY OF THE INVENTION

According to the present invention, there is provided a method and an apparatus for marking indicia made from a few number of opaque, dot-shaped marks in the volume of gemstones, these gemstones being preferably diamonds. The constituent marks of the indicium are engraved preferably at the same depth below the surface of a major cut-and-polished facet of a diamond, this facet being preferably the table of the diamond. As a result, gemstones mounted in any type of settings could be marked. The inscription of each individual mark is performed using a protocol aimed specifically at forming a mark with the desired size by exposing the surface of the gemstone to the smallest quantity of femtosecond laser pulses, each pulse carrying an energy that is generally well below the energy threshold for inducing permanent structural modifications in a perfect diamond crystal lattice. The depth at which the marks are inscribed is controlled through the focusing of the femtosecond laser beam. The exact focusing arrangement is also selected to mark in the volume of a gemstone workpiece while maintaining the optical fluence level (energy per unit area) at the surface of the workpiece well below the surface damage threshold of the material. Marking in the volume is then possible without causing any irreversible optical damage to the outer surface of the gemstone. Previous experimental investigations reported on by some groups about the structural changes in the bulk of a diamond substrate when exposed to a train of femtosecond laser pulses have shown that the marks are generally made up of a quite different elemental form of carbon. The microstructures created therein are then substantially opaque to visible light. Surprisingly, such opaque dot-shaped marks can be made undetectable with the unaided eye or when using an optical instrument having a 10× magnification even if they are inscribed at depths of only a few hundreds μm below the surface of the table. It suffices to exert a tight control along with a judicious selection of some key parameters of the marking process such as the energy per pulse, the effective numerical aperture of the focusing objective, the duration of the laser pulses and the spatial quality of the laser beam to get dot-shaped marks with diameters that do not exceed a few μm, and which are preferably less than 5 μm.

A primary aspect of the invention is that opaque dot-shaped marks can be inscribed in the bulk of a diamond by using femtosecond laser pulses having an energy well below the threshold energy required to inscribe within a diamond crystal lattice of the highest quality, i.e., a crystal having virtually no defects or impurities. Writing permanent marks in the volume of such a diamond piece requires some care since the required optical fluences are susceptible to cause damages at the surface of the workpiece well before succeeding in marking within the bulk. The exposure of a highly valued gemstone to laser pulses having potentially "hazardous" energy levels can be frequently avoided by benefiting from the presence of impurities and defects randomly distributed in the volume of natural diamonds, including those of the highest quality. These impurities and defects of various natures favor the creation of dark and opaque regions when exposed to femtosecond laser pulses with energies substantially lower than the threshold energy of the otherwise perfect material. The random spatial distribution of those defects and impurities in common natural diamonds is at the origin of the stochastic character observed in the previous attempts at marking in a consistent and reproducible manner in the bulk of such diamonds. It is another important aspect of the present invention to account for the spatially varying concentration of defects and impurities in natural diamonds by devising a coding scheme in which the identification data is encoded within the relative positions of a few number of marks, which define the indicium.

Despite of the typical diameter of the dot-shaped marks that should be in the range of a few μm, the opacity of these marks when formed in a diamond allows them to be imaged with suitable contrast by a low-cost optical reading device. The reading device comprises essentially a commodity microscope objective of low numerical aperture that relays enlarged images of the whole engraved indicium to the plane of a CCD sensor for image capture. The images are then processed by a processing means for detection of the plurality of marks that form the indicia followed by the subsequent decoding of the identification data encoded in the indicia. The light illumination system of the optical reading device enhances further the contrast of the images of the engraved marks by taking advantage of the bottom facets of the gemstone, which act as efficient light reflectors. A result of all the above recited aspects relating to the optical reading device is the simplicity of construction of this device, its ease of operation by a user who is neither gemmologist nor microscopist, and its low fabrication cost that makes it affordable to every jewellery store.

In one aspect, the invention comprises a method for adaptive control of the creation of indicia in the bulk of a gemstone specimen using a series of laser pulses in the femtosecond range focused below the surface of the specimen, the indicia identifying the specimen without affecting the surface of the specimen and being invisible under 10× magnification, the method comprising the steps of predetermining characterizing features of the indicia to be created; executing a predetermined marking protocol for the series of laser pulses using parameters selected from among the group comprising wavelength, pulse duration, number of pulses, repetition rate, energy per pulse, numerical aperture of focusing optics and target coordinates; automatically monitoring the creation of the indicia as the protocol is being executed; and automatically interrupting further execution of the protocol when the monitoring reveals that the indicia exhibits the characterizing features.

In another aspect, the invention comprises an adaptive control method for controlling the application of indicia in the bulk of a gemstone specimen using a series of laser pulses in the femtosecond range focused below the surface of the specimen, the indicia identifying the specimen without affecting the surface of the specimen and being invisible under 10× magnification, comprising the steps of, under control of a Processing unit, generating an identification code for association with the specimen; determining a characteristic pattern for a plurality of indicia corresponding to the identification code; under control of the processing unit, executing a marking protocol for the series of laser pulses by applying the pulses to attempt to sequentially create each of the indicia according to the characteristic pattern; and controlling the processing unit such that if execution of the protocol creates one but not all of the indicia according to the characteristic pattern, the processing unit causes the generation of a new identification code corresponding to a new characteristic pattern that is consistent with those of the indicia that have been successfully created, and if required the processing unit executes a marking protocol to create additional indicia to attempt to complete the new characteristic pattern.

In yet another aspect, the invention comprises a gemstone authenticating system comprising: marking apparatus for applying patterns of indicia in the bulk of gemstones using a series of ultrashort laser pulses focused below the surface of gemstones, the indicia being invisible under 10× magnification, the marking apparatus further comprises an imaging optical set-up for assessing the creation of indicia in real time; a database uniquely associating an identification code with each of the patterns of indicia; a plurality of reading apparatus associated with a plurality of remote locations for detecting the patterns of indicia; and a processing unit configured to communicate with the marking apparatus, the database and the reading apparatus, the processing unit being configured to: control the operation of the marking apparatus according to the status of creation of indicia; to adapt parameters for the series of laser pulses according to an assessment of the creation of indicia in real time; and to communicate to the database the successful application of a pattern of indicia.

In another aspect, the invention comprises an adaptive control method for controlling the creation of indicia in the bulk of a gemstone specimen, the indicia identifying the specimen without affecting the surface of the specimen and being invisible under 10× magnification, comprising the steps of establishing a marking protocol for an ultrashort laser pulse marking system, the protocol comprising a plurality of predetermined sets of parameters, each set comprising parameters selected from among the group comprising wavelength, pulse duration, number of pulses, repetition rate, energy per pulse, numerical aperture of focusing optics, and target coordinates; attempting to create an indicium by executing a first set of parameters determined by the protocol; automatically assessing whether an indicium was created using the first set of parameters; if an indicium was not created, automatically attempting to create an indicium according to a second set of parameters determined by the protocol.

In another aspect, the invention comprises apparatus for applying indicia in the bulk of gemstones, the indicia identifying the gemstones and being invisible under 10× magnification, comprising a laser system for focussing laser pulses of less than 100 femtoseconds at selected depths below the surface of a gemstone; memory means containing a marking protocol comprising parameters for the operation of the laser system, the parameters being predetermined and selected from among the group comprising pulse duration, number of pulses, repetition rate, energy per pulse and numerical aperture; a CPU for controlling the operation of the laser system according to the marking protocol; and an automatic process monitoring unit for assessing the creation of each indicium after each pulse.

In yet another aspect. the invention comprises a diamond specimen comprising at least three sub-surface indicia artificially inscribed therein for identifying the specimen, and wherein the at least three indicia are coded as a spatial arrangement of localized areas wherein each of the localized areas exhibits optical characteristics that are different from those surrounding the localized area, each of the indicia being invisible under 10× magnification and being smaller than 3 µm in any dimension.

In another aspect, the invention comprises an adaptive control method for controlling the creation of indicia in the bulk of a gemstone specimen, the indicia identifying the specimen without affecting the surface of the specimen and being invisible under 10× magnification, using a series of laser pulses in the femtosecond range and focused below the surface of the specimen, comprising the steps of predetermining characterizing features of the indicia to be created; under control of a processing unit, generating an identification code for association with the specimen; determining a characteristic pattern for a plurality of indicia corresponding to the identification code; executing a predetermined marking protocol for the series of laser pulses to attempt to sequentially create each of the indicia according to the characteristic pattern, using parameters selected from among the group comprising wavelength, pulse duration, number of pulses, repetition rate, energy per pulse, numerical aperture of focusing optics and target coordinates; automatically monitoring the creation of the indicia as the protocol is being executed; controlling the processing unit such that if execution of the protocol creates one but not all of the indicia according to the characteristic pattern, the processing unit causes the generation of a new identification code corresponding to a new characteristic pattern that is consistent with those of the indicia that have been successfully created, and if required the processing unit causes execution of a marking protocol to create additional indicia to attempt to complete the new characteristic pattern; automatically interrupting further execution of the protocol when the indicia exhibits the characterizing features; and upon completing the creation of the characteristic pattern of indicia or the new characteristic pattern of indicia, recording the identification code or the new identification code, as the case may be, in a database.

In yet another aspect, the invention comprises a method for adaptive control of the creation of indicia in the bulk of a gemstone specimen using a series of laser pulses in the femtosecond range focused below the surface of the specimen, the indicia identifying the specimen without affecting the surface of the specimen and being invisible under 10× magnification, comprising the steps of predetermining characterizing features of the indicia to be created; undertaking the execution of a predetermined marking sequence of the laser pulses using parameters selected from among the group comprising wavelength, pulse duration, number of pulses, repetition rate, energy per pulse and numerical aperture of focusing optics; monitoring the creation of, the indicia as the sequence is being executed; and immediately interrupting the continued execution of the sequence when the monitoring reveals that the indicia exhibits the characterizing features.

BRIEF DESCRIPTION OF THE DRAWINGS

The invention will be further appreciated by reference to the detailed description of the preferred embodiment in conjunction with the drawings thereof, in which.

DETAILED DESCRIPTION OF THE PREFERRED EMBODIMENTS

Outline of a Gemstone Authentication System

Figure 2:
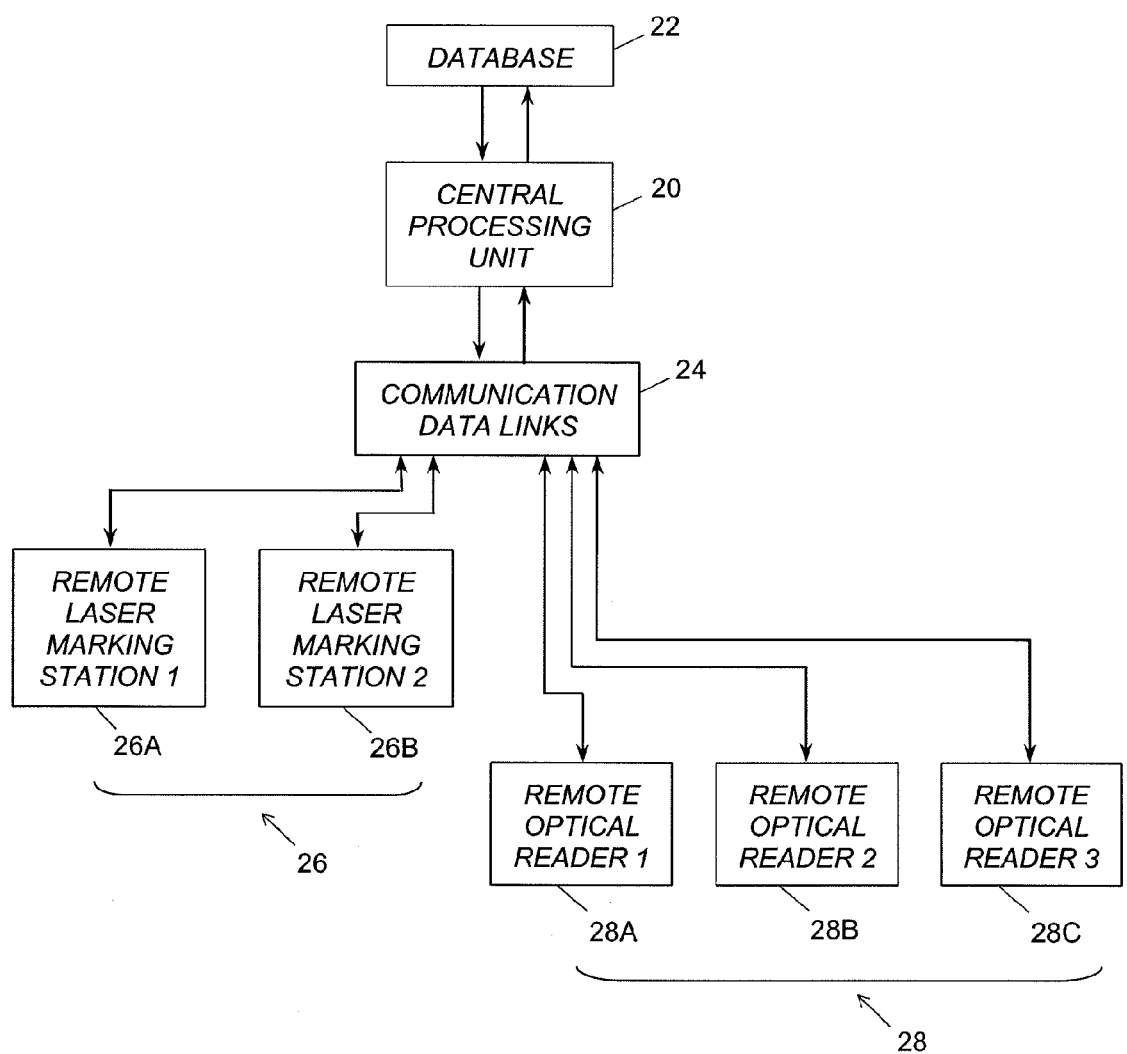
FIG. 2 is a simplified block diagram of a complete system for the marking and authentication of gemstones.

The various objects of the present invention as recited in the section OBJECTS OF THE INVENTION relate to methods and apparatuses that found their primary use in a system for the authentication of gemstones by means of indicia engraved in their volume. FIG. 2 is a simplified block diagram showing an embodiment of a gemstone authentication system. The heart of the system is the central processing unit (CPU) 20, which is essentially a computer that controls the operation of the numerous remote units connected to it through communication data links 24. A primary task of the CPU 20 is to manage the requests for accessing to the information stored in the database 22 as well as to control the storage of new data records in the database registry. The data stored in the database 22 consist mainly of the identification record associated to each gemstone that has been marked. A record includes the numerical data stream that corresponds to the identification code engraved in the gemstone along with other relevant information such as a summary of the intrinsic properties of the gemstone (i.e., its grading report), its current owner, the record of previous ownership, the producer of the gemstone, and the mining site from which it originates.

The remote units that form part of the gemstone authentication system fall within two major groups. The first group includes the remote laser marking stations 26, whose operation is under the control of the CPU 20. For the sake of simplicity, only two marking stations 26A and 26B have been depicted in FIG. 2. However, an actual authentication system would be made up of a larger number of laser marking stations that could be conveniently distributed over the whole geographical area to be covered. The second group includes the remote optical readers 28 whose operation is under the control of the CPU 20 as well. Only three optical readers 28A, 28B and 28C are illustrated in FIG. 2, but in practice these devices could be found at numerous places, which include jewellery retail stores, police headquarters, and diamond trading offices. The optical readers 28 serve primarily to detect the presence of an authentication indicium engraved in the bulk of a gemstone under examination, and then to provide input data (essentially an image) to the CPU 20 for the proper identification of the gemstone. Each remote laser marking station 26 also includes its own optical reader 28 to allow registration of each gemstone in the database 22 of the authentication system immediately after its marking.

Description of a Preferred Embodiment for the Laser Marking Station

Figure 3:
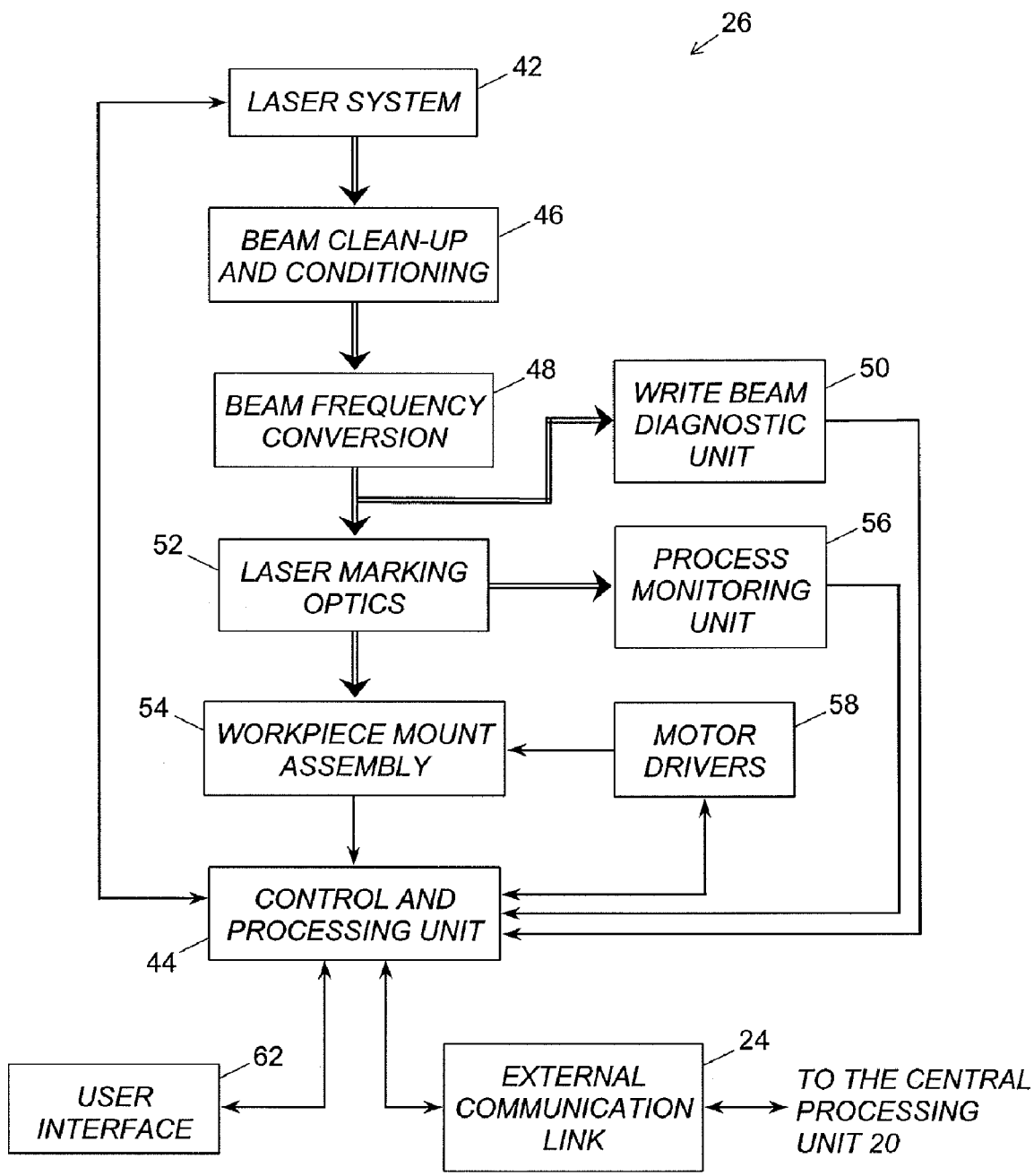
FIG. 3 is a block diagram showing the main units and assemblies of a laser marking system in accordance with a preferred embodiment of the present invention.

The roles played by the various constituent units of a preferred embodiment for the laser marking station 26 will be better understood by referring to the simplified block diagram depicted in FIG. 3. The arrows drafted with a double line in FIG. 3 represent a laser beam, while those made up of a single line stand for electrical connections required for various purposes, such as the exchange of data, the transmission of command and control signals, and the electrical power supply of some units. Each laser marking station 26 comprises its own control and processing unit 44, which can be implemented via a personal computer configured for industrial use. The control and processing unit 44 controls the operation of most of the constituent units of the laser marking station 26, either from commands entered by an operator via the user interface 62 or from commands issued from the operation software of the CPU 20 of the authentication system and transmitted through the external communication link 24.

The laser system 42 generates a laser beam in the form of pulses of ultrashort duration and emitted in repetitively pulsed regime. The operation of the method of the present invention requires that the duration of the laser pulses be in the femtosecond range. More specifically, the pulse duration should not exceed a few hundreds fs and, preferably, it should be lower than about 100 fs. Representative examples of femtosecond laser systems are those that include a Titanium-Sapphire (Ti:Sapphire) solid-state gain medium that is optically pumped by semiconductor laser diodes. These laser systems emit laser beams having a wavelength typically in the near infrared region, and particularly in the range from 750 nm to 800 nm. Ti:Sapphire femtosecond laser systems can be implemented in the form of a single oscillator that provides laser pulses carrying energies in the nJ range and emitted at repetition rates typically in the tens of MHz (megahertz). However, laser pulses with energies up to a few mJ can be obtained by coupling the output of the laser oscillator to a regenerative optical amplifier. An advantage of the method of the present invention is to enable the marking of gemstones with laser pulses having energies as low as a few tens of nJ, so that the use of a regenerative optical amplifier is not absolutely required when using a Ti:Sapphire laser system. This advantage results in a substantial simplification of the hardware along with a lower procurement cost for the whole laser system. Because the efficiency of the laser marking process depends on the spatial quality of the write laser beam emitted by the laser system 42, the beam clean-up and conditioning unit 46 can perform a spatial filtering of the beam. This unit also serves to adjust the spatial characteristics (i.e., the divergence and transverse beam size) of the laser beam in order to maximize the efficiency of the frequency conversion process performed by the frequency conversion unit 48. This process consists essentially in doubling the optical center frequency of the laser beam, so that an initially 775-nm wavelength laser beam can be converted to a 388-nm wavelength beam. The frequency conversion unit 48 is facultative for marking in some gemstone materials, and it relies on second harmonic generation (SHG) schemes well known in the art. FIG. 3 shows that the frequency-converted laser beam then passes through laser marking optics 52 that enables a tight focusing of the laser beam at some depth below the input surface of a gemstone secured within the workpiece mount assembly 54. The control and processing unit 44 controls the translation of the workpiece mount assembly 54 via dedicated motor drivers 58, in order to mark at various locations inside of the gemstone.

The spatial characteristics of the write laser beam are preferably monitored and controlled in real time by the control and processing unit 44 through the data and images generated by the write beam diagnostic unit 50. The write beam diagnostic unit 50 is required to allow early detection of any change in the laser beam properties or any failure in the operation of the laser system. Both types of events could adversely affect the marking process or, in a worst-case scenario, cause irreversible damages to the gemstone exposed to the write laser beam. Finally, an aspect of the present invention is to provide a laser marking protocol that relies on the real-time monitoring of the growth of the dot-shaped marks in the volume of gemstones. This monitoring is performed via the images and data provided in real time by the process monitoring unit 56. This unit makes use of some optical components of the laser marking optics 52 to get appropriate light signals from the region wherein a mark is currently building up.

Figure 4:
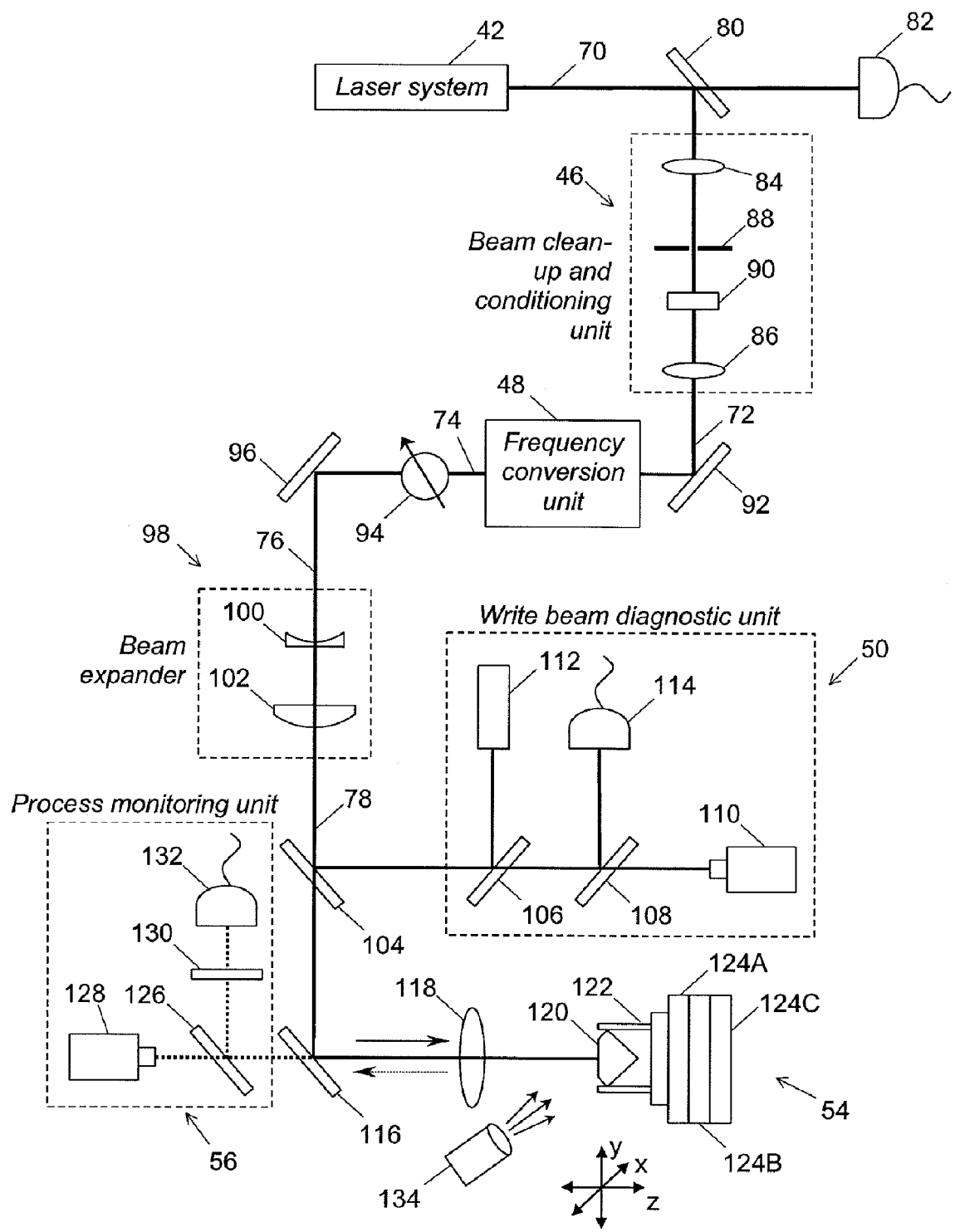
FIG. 4 is a schematic view of the various optical components and constituent units of a laser marking system in accordance with a preferred embodiment of the present invention.

FIG. 4 is a layout that shows a preferred arrangement for the optical components that form part of the various units required for the operation of a laser marking station in accordance with the method of the present invention. In this figure, the thick solid lines depict the optical paths of the laser beams propagating in the optical set-up. A small fraction of the laser beam 70 emitted by the femtosecond laser system 42 is transmitted through a beamsplitter plate 80 and then hits the photosensitive surface of an optical power meter 82. The reading from the power meter 82 is fed to the control and processing unit 44 (not shown in the figure) to allow continuous monitoring of the operation of the laser source 42 through the measurement of the average optical power of its output beam 70. The main part of the laser beam 70 is reflected by the beamsplitter 80 and then passes through the beam clean-up and conditioning unit 46. In a preferred embodiment, the unit 46 comprises two converging lenses 84 and 86 of suitable focal lengths, an iris diaphragm 88 and a mechanical shutter 90 whose opening is remotely controlled by the control and processing unit 44. The iris diaphragm 88 is placed at the focal plane of the lens 84 to provide a spatial filtering action controlled by the diameter of its aperture. The mechanical shutter 90 allows the transmission of a pulse train of limited duration that includes a predetermined number of laser pulses, this number being dictated by the specific laser marking protocol currently underway. The spatially filtered laser pulse train 72 is then reflected by a high-reflectivity plane mirror 92 onto the input aperture of the frequency conversion unit 48. The frequency conversion relies on second-harmonic generation that takes place in some optical crystals without inversion symmetry such as BBO (Beta Barium Borate), LBO (Lithium Triborate), KTP (Potassium Titanyl Phosphate) or KDP (Potassium Di-hydrogen Phosphate). The energy per pulse of the frequency-converted laser beam 74 is then set at the desired value through a signal from the control and processing unit 44 that is forwarded to the adjustable optical attenuator 94. This attenuator can be built, for example, from a half-wave retarder plate mounted in a rotation stage and followed by a polarizing beamsplitter cube, this configuration being well known in the art. The proper operation of a variable optical attenuator 94 designed in this way requires that the input laser beam 74 be linearly polarized.

The laser beam having the desired energy per pulse is then reflected by a high-reflectivity plane mirror 96 before reaching a beam expander 98. FIG. 4 illustrates a beam expander of Galilean type, which is made up of an input diverging lens 100 and an output converging lens 102. The focal lengths of the lenses 100 and 102 are chosen so that the transverse beam size of the laser beam 76 is properly enlarged to fill in the entrance pupil of a focusing objective 118 without excessive clipping. An adequate filling of the entrance pupil enables the focusing objective 118 to operate at its full numerical aperture. The major part of the transversely expanded laser beam 78 passes through a beamsplitter plate 104 and is then reflected by a dichroic beamsplitter plate 116 to impinge on the entrance pupil of the focusing objective 118. Note that the beam expander 98 and the focusing objective 118 are the two basic elements of the laser marking optics 52 as depicted in the block diagram of FIG. 3.

The distance between the output aperture of the focusing objective 118 and the input surface of the gemstone 120 to be marked is adjusted until the plane of best focus of the focused laser beam is obtained at the desired depth in the volume of the gemstone 120. The gemstone 120 is secured within a workpiece mount assembly 54 that comprises preferably a holder 122 adapted to the size and shape of the gemstone, the holder 122 being mounted on a stack of three motorized linear translation stages 124A, 124B, and 124C. Two of the translation stages displace the gemstone along the X and Y transverse directions, while the third translation stage moves the gemstone along the Z direction, parallel to the optical axis, in order to adjust precisely the distance between the focusing objective 118 and the input surface of the gemstone 120. The translation stages 124A, 124B, and 124C are controlled by the control and processing unit 44 of the laser marking station via the motor drivers 58, as depicted in FIG. 3.

FIG. 4 shows that a part of the transversely expanded write laser beam 78 is reflected by the beamsplitter plate 104 toward the write beam diagnostic unit 50. In a preferred embodiment this unit comprises three optical channels, each of them being used to monitor a specific characteristic of the write laser beam 78. A first channel includes a CCD camera 110 that captures images of the transverse beam intensity distribution in the plane of the camera sensor, while a second channel contains a laser pulse counter 112. Finally, a third optical channel measures the time-averaged energy per pulse through the conversion of the reading from an optical power meter 114, accounting for the reflection and transmission factors of the various beamsplitter plates located along the beam path. The beamsplitter plates 106 and 108 serve to direct parts of the write laser beam 78 toward the various optical channels of the write beam diagnostic unit 50.

FIG. 4 also illustrates a preferred embodiment for the process monitoring unit 56. The path of the light that is recorded by this unit is depicted by the dotted line segments in FIG. 4. Through the use of optical instruments such as a CCD camera 128 and a fast photodetector 132, this unit serves to analyze images and light signals coming from the specific region that is currently being marked in the bulk of the gemstone 120. For example, real-time images of this region can be captured by the CCD camera 128. In this arrangement, the focusing objective 118 is an integral part of the camera objective that relays a magnified image of the region of interest onto the plane of the CCD sensor of the camera 128. Images presenting adequate contrast can be obtained by properly illuminating the gemstone 120 with a light illuminator device 134 as the marking proceeds. Likewise, the fast photodetector 132 can be used to record the rapid pulses of light (plasma radiation) that are generated when a diamond material is subjected to local structural changes caused by the interaction of the material with the intense ultrafast pulses of the write laser beam. A bandpass optical filter 130 inserted across the path of the light beam directed toward the fast photodetector 132 enables spectrally-selective detection of the light radiated as the internal structural changes set in. The beamsplitter plate 126 directs parts of the light toward the two optical channels implemented in the illustrated embodiment for the process monitoring unit 56.

Numerous variations in the design of the laser marking apparatus as described above can be imagined without departing from the spirit of the present invention. For example, the frequency conversion unit 48 is facultative for marking in the bulk of gemstones but, in some instances, a write laser beam of shorter wavelength provides further control of the growth of the dot-shaped marks. Likewise, the spatial filtering performed by the beam clean-up and conditioning unit 46 is not required when the laser beam 70 right at the output of the femtosecond laser system 42 has a satisfactory spatial quality. The optical set-up depicted in FIG. 4 can be modified to avoid the use of the plane mirrors 92 and 96, although such mirrors are useful for the alignment of the write laser beam. Finally, several lenses present in the optical set-up illustrated in FIG. 4, and including the focusing objective 118, could be replaced by curved mirrors.

Description of a Preferred Embodiment for the Optical Reader

Figure 5:
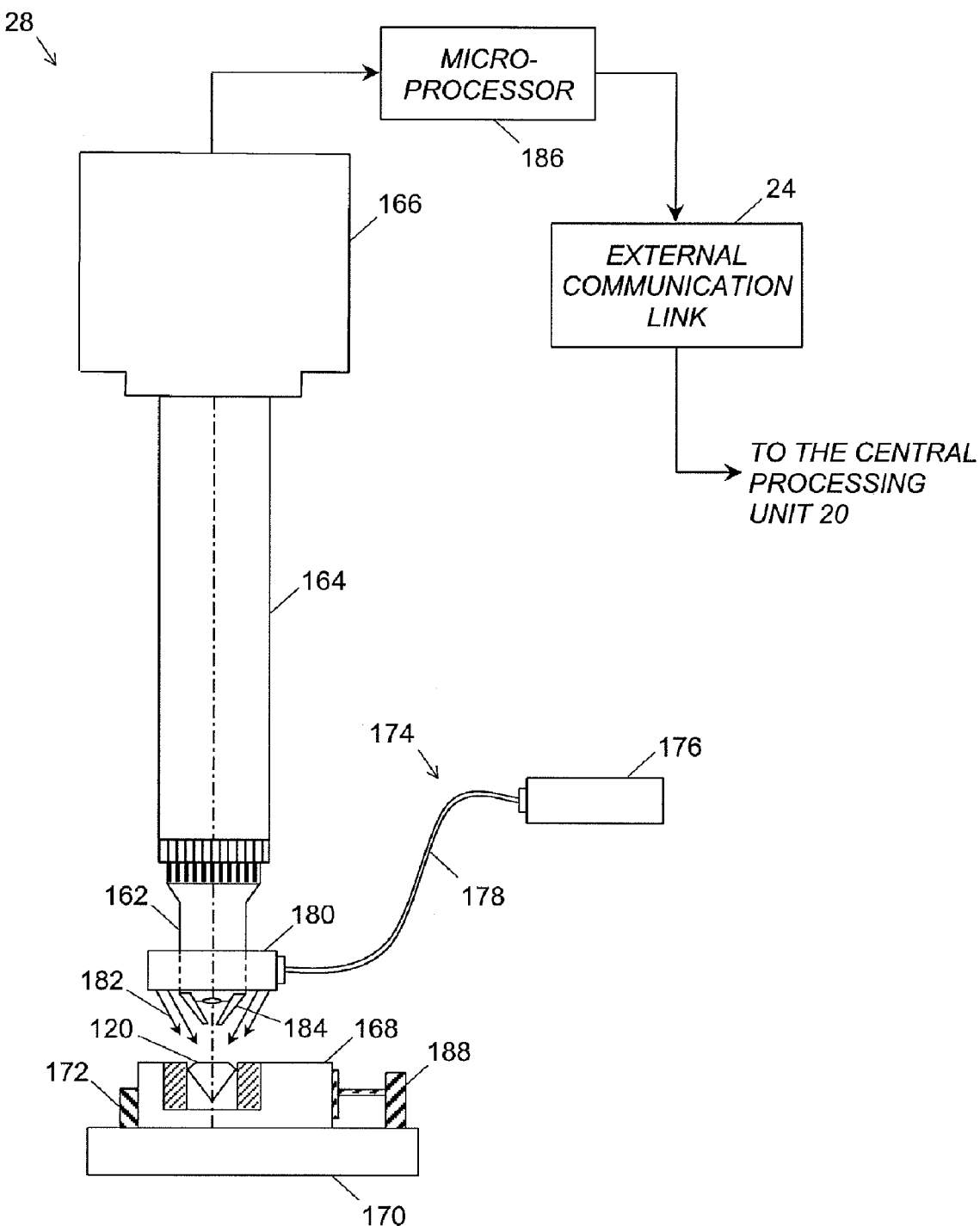
FIG. 5 is a side elevational view of an optical reader that provides images of an indicium engraved in the volume of a gemstone, in accordance with a preferred embodiment of the present invention.

FIG. 5 shows a side elevational view of a preferred embodiment for an optical reader unit 28 that forms part of the complete gemstone authentication system as depicted in the block diagram of FIG. 2. The design of the optical reader 28 revolves around a staring imager configuration wherein the indicium engraved in the volume of the gemstone 120 is imaged onto the array sensor of a CCD camera 166. As a consequence, there is no raster scanning of a probe laser beam upon the surface of the gemstone 120. A microprocessor 186 receives the image data signals from the CCD camera 166, and then processes the image data files before forwarding them to the central processing unit 20 of the authentication system via a communication data link 24. The indicium engraved in the volume of the gemstone 120 is imaged with adequate transverse magnification on the array sensor of the CCD camera 166 by an optical system made up basically of a microscope objective 162 fit to an extension tube 164. The microscope objective 162 is preferably a standard commodity objective designed for use with a 160-mm tube length. The exact length of the extension tube 164 is then chosen accordingly. The magnified images of indicia having convenient overall sizes were found to be well suited to the size of most CCD array sensors by selecting a microscope objective 162 that provides a magnification in the range of 10× to 20×. This range of magnification offers a satisfactory transverse resolution as well as a convenient working distance.

Images with adequate contrast can be obtained from the CCD camera 166 by using a reflected-light illumination scheme that provides bright-field illumination of the marks engraved in the gemstone 120. A reflected-light illumination means basically that the illuminating light is incident onto the specimen (here the gemstone 120) from the top input surface (here the table of the gemstone). In fact, a reflected-light illumination scheme was required to allow the optical reader 28 to operate even with gemstones mounted in a setting, for which an illumination light incident from the bottom of the specimen is ruled out. The peculiar shapes of gemstones also prevent from illuminating them from the bottom. An aspect of the reflected-light illumination scheme as devised for this preferred embodiment of the optical reader 28 is the annular shape of the illumination light beam when it gets incident on the table of the gemstone 120. This light beam is represented by the arrows 182 in FIG. 5. The diameter of the illumination annulus in the plane of the table is chosen wide enough to avoid any direct illumination of the indicium when this latter is in the center region of the field of view of the optical reader. Upon entering into the gemstone 120, the illumination light then propagates downward before being internally reflected upward along various directions by the cut and polished facets located on the lower portion of the gemstone 120. As a result, the dot-shaped marks that form the indicium are lighted from the bottom, thus appearing typically in the images as dark black spots over a bright background. A ring-shaped illuminator head 180 whose inner diameter fits to the microscope objective 162 delivers the illumination light beam 182 with an annular transverse shape. Ring illuminator heads are available in various sizes from most vendors of equipment for video imaging and machine vision applications.

In the preferred embodiment depicted in FIG. 5, a broadband fiber optic illuminator 176 provides the illumination light and a flexible fiber optic light guide 178 mated to the illuminator output aperture transmits the illumination light to the ring-shaped illuminator head 180. The illuminator 176, the fiber optic light guide 178 and the ring-shaped illuminator head 180 form together a complete light illumination unit 174. Taking advantage of the reflected-light illumination scheme as depicted in FIG. 5, the contrast of the images can be enhanced further by using means for preventing parts of the illumination light beam 182 from reaching the region of the gemstone input surface that lies directly over the engraved indicium. In this purpose, a conical light shield 184 is mated to the lower end of the microscope objective 162 to block any illumination light 182 that would otherwise reach the center portion of the gemstone input surface. The aperture at the bottom end of the conical light shield 184 is set wide enough so that the microscope objective 162 can operate at its nominal numerical aperture.

The gemstone 120 to be examined by the optical reader 28 is secured within a holder 168, this holder being placed on a support base 170. The holder 168 can be designed to enable a correct positioning of the gemstone 120 so that the indicium, when engraved in the center region of the table, will appear nearly centered on the field of view of the optical reader 28. A separate instrument (not shown in the figure) for centering the gemstone in the holder 168 can be built up using for example a low-power magnifier containing a graduated reticule, two manual micrometric translation stages and a base plate. Once the gemstone is correctly centered on the reticule of the magnifier, the magnifier is then removed and the remaining assembly is then slide on the support base 170 until it abuts on three separate reference stops 172, only one of them being shown in FIG. 5. The holder can then be held firmly in place with a quick release clamp 188. Finally, as part of the procedure for installing the gemstone 120 in the holder 168, the plane of the table of the gemstone is made coincident with a reference horizontal surface of the holder assembly. This step is to ensure that the vertical position of the gemstone is correctly adjusted to readily bring the images of the engraved indicium into focus.

Only loose, unmounted gemstones can be secured within a holder 168 such as the specific one depicted in FIG. 5. However, modifications to some parts of the holder can be readily carried out by an individual skilled in the art to allow reading of indicia engraved in set gemstones, such as gemstones mounted in rings, earrings, pendants and bracelets. As a result, the optical reader 28 is normally operated with a set of holders 168 to accommodate gemstones mounted in a variety of settings.

The assembly of the optical reader 28 can be housed in a variety of ways. For example, all of the constituent components depicted in FIG. 5, including the micro-processor 186 and related electronics, can be enclosed in a single protective housing or cabinet. The cabinet has preferably a nice-looking appearance suited for environments such as the front desk of jewellery retail stores. A door opening made in the front sidewall of the cabinet allows the operator to insert the gemstone holder 168 in the assembly to set the gemstone 120 in correct registration with the optical axis of the optical reader. The front sidewall of the cabinet comprises a user interface made up of a liquid-crystal display and a control panel. The assembly of the optical reader 28 can also be packaged in the form of a remote hand-held probe head connected to a control and interface unit. This hand-held device comprises the microscope objective 162, the extension tube 164, the CCD camera 166 and the complete light illumination device 174, all of these components being available in small-sized format to allow their packaging into a convenient device that could be held with the hand. For example, the light illumination device 174 can be implemented from a compact ring-shaped illuminator in which light is generated by an array of solid-state light-emitting diodes. Likewise, a custom microscope objective 162 can be designed to image an object in a plane closer than the standard 160-mm distance mentioned previously. The hand-held configuration offers the advantage of not requiring the use of the gemstone holder 168 and of the related parts 170, 172, and 188 since the gemstone 120 is simply brought into contact with the frontal end of the probe head. In this purpose, the frontal end comprises a flat plate made up of a hard, transparent material on which the table of the gemstone is set in close contact. The flat plate serves to place the table of the gemstone at a correct working distance from the frontal end of the microscope objective. Alignment marks engraved onto the flat plate facilitates the centering of the gemstone relative to the optical axis of the reader. In this embodiment, the probe head is grasped with one hand while the gemstone 120 is held with the other hand, either by using tweezers for a loose gemstone or by holding mounted gemstones via their settings.

Inscribing Marks in the Bulk of Gemstones

Figure 6:
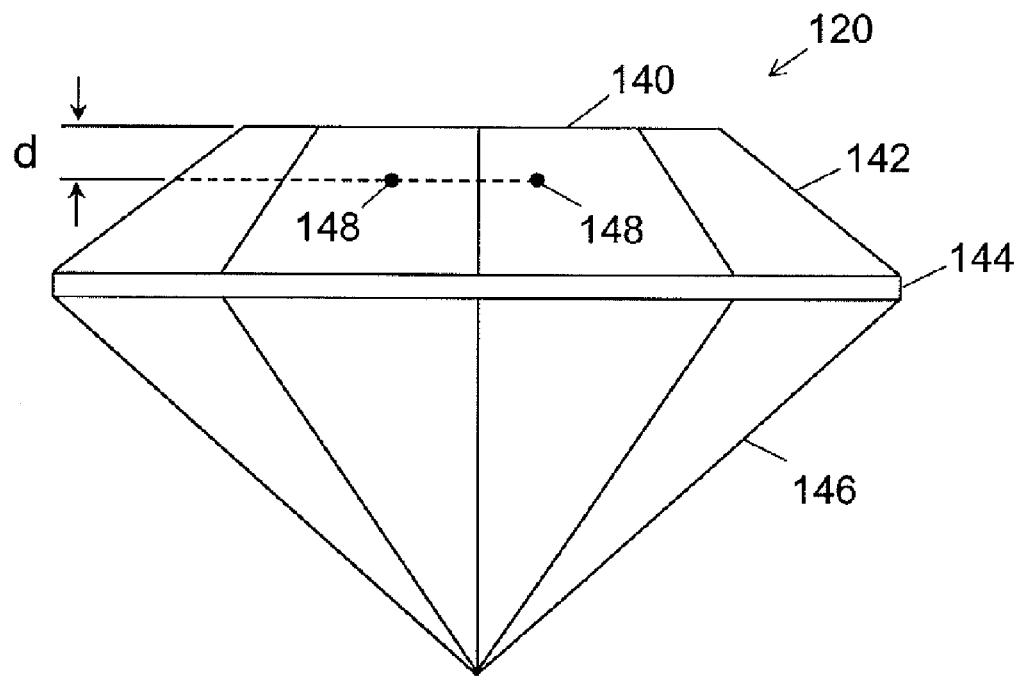
FIG. 6 is an elevational side view of a diamond gemstone in which two distinct marks have been inscribed below the surface of the table.

FIG. 6 shows a side elevational view of a gemstone 120 in which two distinct dot-shaped marks, both having the same reference numeral 148, have been engraved in its bulk. In particular, FIG. 6 depicts a diamond having a round brilliant cut. The table of this diamond gemstone is the upper horizontal flat surface 140 upon which the write laser beam is made incident during marking. A gemstone having a round brilliant cut also comprises a crown 142 and a pavilion 146, both parts being made up of several facets, not shown in the figure. The girdle 144 is the peripheral band located between the crown 142 and the pavilion 146.

Figure 7:
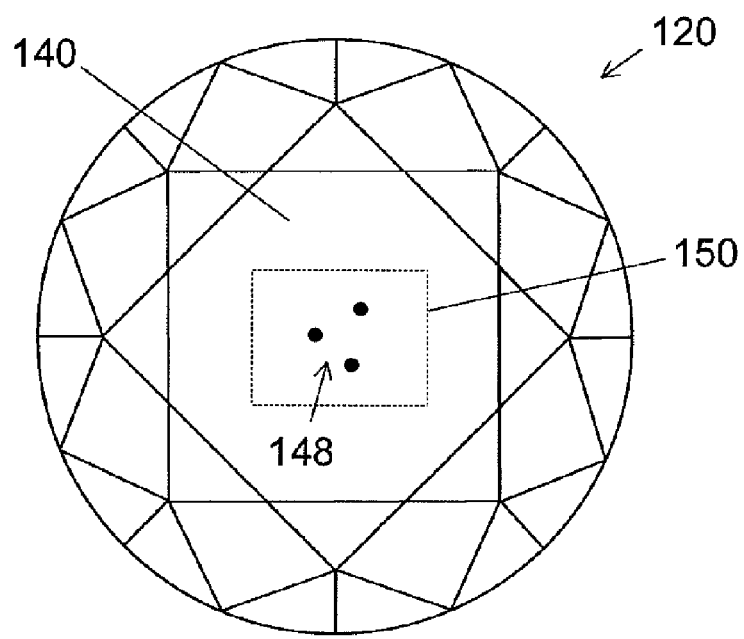
FIG. 7 is an elevational top view of diamond gemstone having a round brilliant cut and in which three distinct marks have been inscribed below the surface of the table and in the vicinity of the center of the table.

A important aspect of the method of the present invention is the marking of dot-shaped marks having a controlled size in the volume of a gemstone such as a diamond. When marking in the volume, it is understood that the surface of incidence (i.e., the table) of the gemstone as well as the portion of the volume of the gemstone material located along the internal trajectory of the write laser beam are by no means altered by the marking process. As a consequence, the laser-induced structural changes that lead to the formation of permanent marks must set in only within a thin slice located at a depth d below the table 140 of the gemstone, as illustrated in FIG. 6. The thickness of the imaginary thin slice is dictated by the overall precision of the process at marking at a nominal depth d below the table 140. For the sake of simplicity, it is generally desired that all of the marks 148 lie at the same depth since it helps in obtaining the entire set of marks in sharp focus in the images captured by the optical reader 28. The marks 148 are distributed in the thin slice according to a pattern that depends on the symbology (encoding scheme) selected for encoding authentication data as well as on the specific identification code attributed to the gemstone. For example, FIG. 7 is an elevational top view of a round brilliant cut gemstone, showing three distinct marks 148 that form the indicium. The rectangle 150 sketched in short-dashed lines delimits the outer contour of the field of view in the object plane of the optical reader 28 designed in accordance with a preferred embodiment of the present invention. This embodiment, as depicted in FIG. 5, calls for marking the indicium in the center region of the table 140.

In a further embodiment of the method, the marks could be inscribed at different depths below the table of a gemstone 120 without departing from the spirit of the present invention, thus leading to the inscription of three-dimensional (3-D) indicia. As compared to their 2-D counterparts, 3-D indicia offer the advantage of having a greater covertness since the constituent marks cannot be brought into focus simultaneously when viewed through an optical instrument whose depth of field is shorter than the range of depths over which the constituent marks have been engraved. However, the greater difficulty in detecting 3-D indicia means that the design of the optical reader 28 as depicted schematically in FIG. 5 must be upgraded to allow imaging of planes located at various depths into the volume of the gemstone. Such an upgrade could be implemented, for example, via a controlled vertical translation of the holder 168. Images would be recorded in sequence by the CCD camera 166 during the vertical movement of the gemstone 120. The whole indicium could then be reconstructed by combining the sub-set of images in which each individual mark is brought into sharp focus, while keeping their relative positions unchanged. The resulting composite image could then be forwarded to the CPU 20 for subsequent decoding of the indicium. This further embodiment of the optical reader 28 offers the advantage of not requiring that the marks be inscribed at very precise depths into the gemstone 120.

FIGS. 6 and 7 greatly exaggerate the relative size of the marks 148 because in practice they must remain undetectable when looking at the table of the gemstone 120 with the unaided eye or with a 10× optical instrument. It is even keenly desired that the marks be difficult to detect when viewed without any previous cue through binocular microscopes of current use in gemmology. The intrinsic opacity of the constituent material of the engraved marks 148 makes their covertness particularly challenging when using the visual aids mentioned above. A key to the covertness of the marks is to implement a laser marking procedure that enables the sub-surface inscription of marks having overall individual sizes that do not exceed about 5 μm, and that are preferably smaller than 2 μm.

Control of the Focusing of the Write Laser Beam into the Gemstone

A significant aspect of the laser inscription of dot-shaped marks with diameters of only a few μm relates to the control of the focusing of the write laser beam into the bulk of the gemstone 120. The focusing of the write laser beam is depicted schematically in FIG. 8. The arrows 152 indicate the gross outer contour of the optical intensity distribution of the write (transversely-expanded) laser beam 78 (see FIG. 4) that propagates along the optical axis 156 before reaching the entrance pupil of the focusing objective 118. Likewise, the arrows 154 depict the corresponding outer contour of the write laser beam that leaves the objective 118 to be tightly focused on a volume located at a depth d below the table 140 of the gemstone 120.

The numerical aperture of the objective 118, which is a measure of the angular spread of the beam exiting from this optical component, must be carefully selected to get the desired beam characteristics in the volume of the gemstone 120. On one hand, the diameter $W_F$ of the laser beam intensity profile at the plane of best focus gets lower when increasing the numerical aperture of the objective. This trend holds in a regime wherein the focused laser beam 154 is not severely distorted by the spherical aberrations that arise during its propagation through the various optical elements of the objective 118. Increasing the numerical aperture of the objective also helps in minimizing the risks of inflicting laser-induced optical damages to the surface of the table 140. This comes from the diameter $W_S$ of the beam intensity distribution in the plane of the table 140 that can be made substantially larger that the corresponding diameter $W_F$ of the beam intensity distribution at the plane of best focus. As a result, the optical fluence (energy per unit surface) at the plane of the table 140 can be well below the fluence required to trigger the development of a dot-shaped mark 148.

Figure 8:
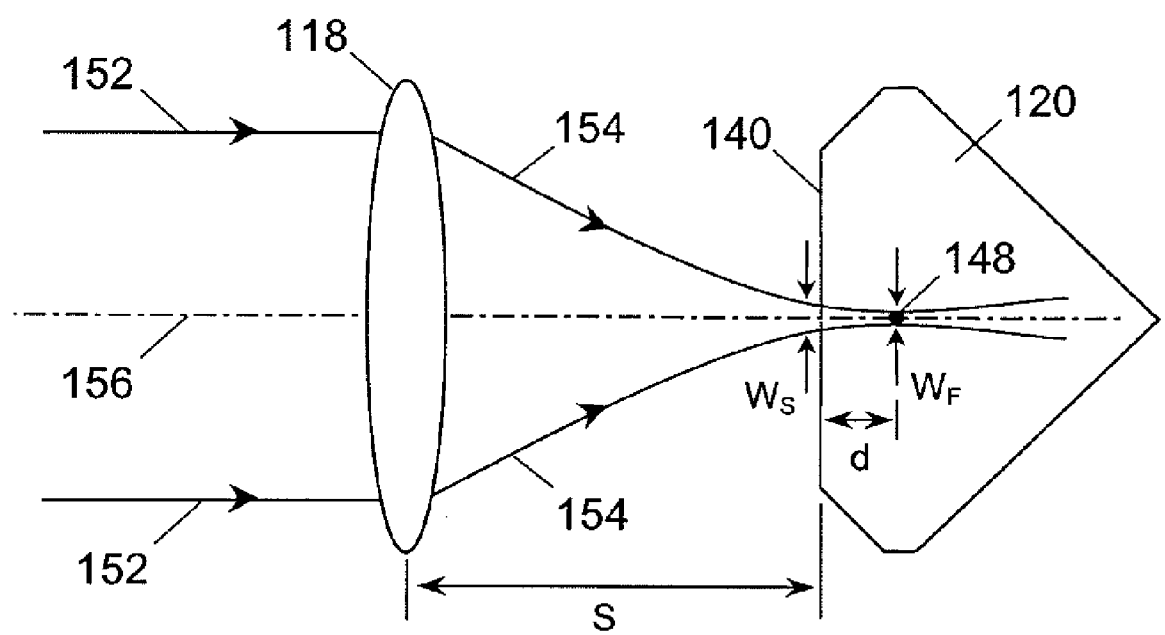
FIG. 8 is a schematic diagram that shows the focusing of the write laser beam into the volume of a gemstone.

On the other hand, using an objective 118 of higher numerical aperture results in a shorter (and possibly inconvenient) working distance S as depicted in FIG. 8, while the focused laser beam can get substantially degraded by any residual optical roughness present on the polished surface of the table 140. In addition, the effects of the spherical aberrations induced by the passage of the write laser beam in the objective 118 must be accounted for when estimating the minimum transverse size $W_F$ of the beam at the plane of best focus. A practical design for a focusing configuration revolves around an objective 118 having a focal length in the range of 5 to 10 mm along with a numerical aperture varying between 0.35 and 0.55. Because of the very tight focusing of the write laser beam, ray tracing calculations that properly account for the precise optical design of the focusing objective 118 must be carried out to get the plane of best focus at the desired depth d below the table 140 along with the desired beam spot size $W_F$ in this plane. The depth d is set preferably in the range from about 200 µm to 700 µm. Inscribing marks deeper below the surface of the table 140 provides a greater covertness for the marks. On the other hand, the longer propagation path of the write laser beam into the gemstone material increases the probability that the beam be perturbed by natural inclusions and other types of inhomogeneities present in the material.

Description of a Preferred Embodiment for the Encoding Scheme

The above paragraphs have detailed some aspects of a method for engraving dot-shaped marks having an overall size that is preferably around 1 µm in the volume of gemstones, with the objective of making each individual mark nearly imperceptible when using visual aids commonly found in the art. Unfortunately, it is readily understood that an indicium could become easily visible if it is made up of an excessive number of opaque dot-shaped marks spread over an area of limited dimensions. Another major aspect of the present invention is then to provide a way for encoding machine-readable identification information in indicia that are formed of only a few individual marks.

Figure 9:
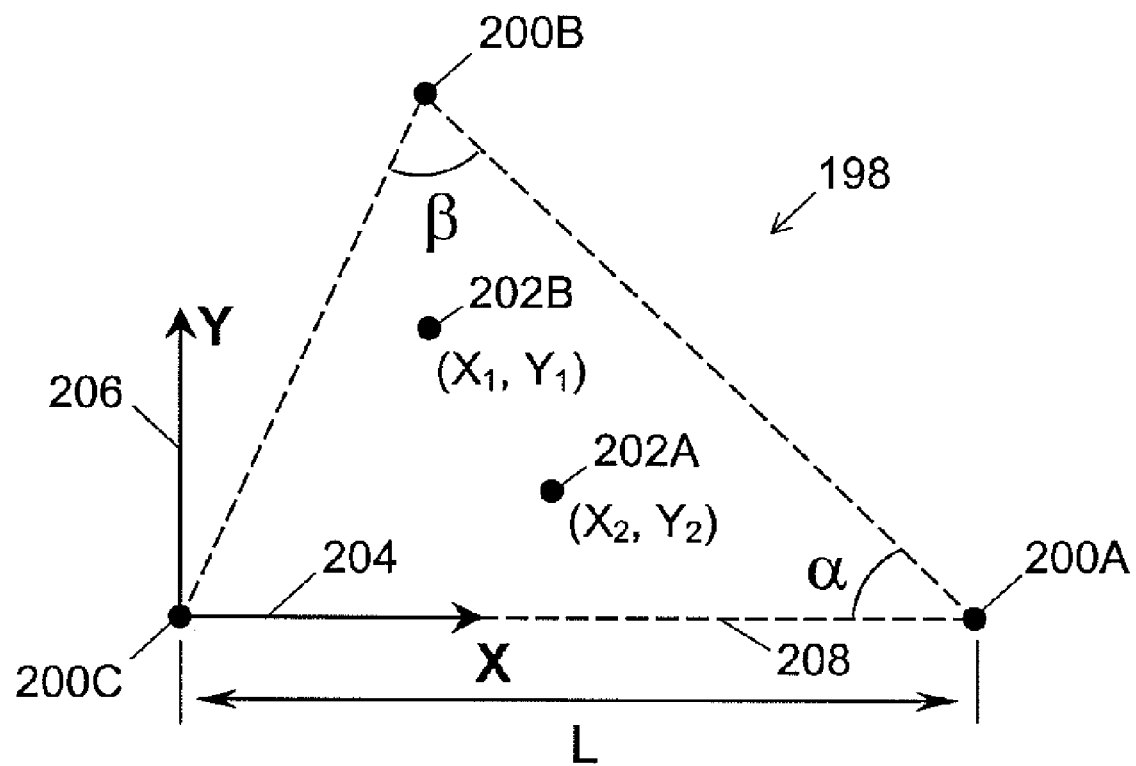
FIG. 9 is a schematic view of an indicium made up of a set of five dot-shaped marks, in accordance with a preferred embodiment of the present invention.

FIG. 9 is a schematic view of an indicium 198 designed according to a preferred encoding scheme of the present invention. The indicium 198 comprises five marks, which can be divided into two groups according to their specific roles in the encoding scheme. Hence, a first group of marks labelled with the reference numerals 200A, 200B and 200C forms the corners of a geometrical figure aimed at allowing faithful recognition of the indicium 198 by a computer software that processes the images provided by an optical reader 28 of the present invention. The specific geometrical figure shown in FIG. 9 is a triangle whose sides are sketched in dashed line. Other geometrical figures can be imagined by including additional marks in the first group without departing from the spirit of the preferred encoding scheme of the present invention. The second group includes the two marks labelled with the reference numerals 202A and 202B, these marks serving solely to encode identification data. Additional marks can be included in the second group as well. In the preferred encoding scheme, numerical data that unambiguously identify the gemstone are encoded from the positions of the dots 202A and 202B, these positions being expressed by the spatial coordinate pairs $(X_1, Y_1)$ and $(X_2, Y_2)$, respectively. Some specific attributes of the triangle shown in dashed line also serve to encode identification data in order to increase the number of different combinations allowed by the encoding scheme. In the example shown in FIG. 9 the values of the two internal angles $\alpha$ and $\beta$ add to the spatial coordinate pairs given above to form the complete identification code attributed to a gemstone. The full numerical identification code obtained from the indicium 198 can then be expressed by the data stream (X1, Y1, X2, Y2, $\alpha$, $\beta$) formed of six elements. The data stream can be lengthened to increase the number of distinct identification codes by including the spatial coordinates associated to additional encoding marks.

At first sight, the presence of the encoding marks 202A and 202B would prevent from performing reliable machine recognition of the indicium 198 because a lot of different triangles can be sketched from the five marks shown in the figure. The recognition software can get rid of this potential difficulty simply by instructing it to retain the triangle that has the longest side, given here by the side 208 of length L shown in FIG. 9. This means that equilateral triangles are ruled out from the preferred encoding scheme. Excluding equilateral triangles also provides a recognition scheme that is invariant under rotation of the indicium 198 in the images obtained from the optical reader 28. Rotation-invariant recognition of the indicium 198 is important because the mark 200C that forms the left-hand end of the largest side 208 of the triangle also defines the origin of the cartesian X-Y reference frame from which the positions of the encoding marks 202A and 202B are referenced. The X-Y reference frame associated to the indicium 198 is illustrated in FIG. 9 by the X axis 204 and the Y axis 206. Referencing the spatial coordinates of the dots 202A and 202B to the position of the dot 200C also ensures that the decoding process is invariant upon translation of the indicium. This advantageous property implies that the indicium 198 needs not to be positioned at a specific location within the surface of the table of the gemstone. Moreover, the indicium needs not to be precisely centered in the images output from the optical reader 28.

The decoding of the identification code encrypted in the indicium 198 is made invariant upon scaling by expressing the spatial coordinates of the encoding marks 202A and 202B relative to the length L of the longest side 208 of the triangle. As a result, the individual spatial coordinates $X_1$, $Y_1$, $X_2$, and $Y_2$ are given by values intrinsically limited to the interval from 0 to 1. Implementing a recognition process that is invariant upon scaling of the images reveals as of great usefulness when those images can be taken with various optical readers 28 equipped with microscope objectives 162 that do not necessarily provide all the same magnification. Furthermore, the exact physical length L of the side 208 does not affect the recognition of an indicium and its subsequent decoding. In practice, the length of the largest side 208 of the triangle is chosen so that the whole indicium 198 can always be fully enclosed within the field of view in the object plane of the optical reader 28, irrespective of the way the indicium is rotated relative to the contour of the field of view. In some cases, however, the overall dimensions of an indicium must be kept relatively small because it is strongly preferable that the whole area delimited by the outer contour of the indicium be free of any naturally-occurring inclusion that could be detected in the images captured by the optical reader 28. Keeping the indicium free of any inclusion is particularly important in cases wherein these inclusions could bear strong resemblance with the engraved marks, thus preventing the recognition software to filter them out from the images before starting the recognition of the indicium.

In another embodiment of the optical reader 28, the magnification of the microscope objective 162 could be precisely calibrated to enable measurement of the actual length L of the longest side 208 of the triangle that serves to recognize the indicium 198. The measured value of L can then be included as a seventh element in the data stream (X1, Y1, X2, Y2, $\alpha$, $\beta$) that constitutes the numerical representation of the identification code encrypted in the indicium 198. Adding the measured value of L as part of the identification codes results in a significantly increased number of distinct combinations allowed by the encoding scheme.

In the preferred encoding scheme, the marks 202A and 202B are always located inside of the triangle that delimits the indicium 198, so that the range of allowable values for their spatial coordinates covers only a limited portion of the maximum interval that spans from 0 to 1. The interval of variation for each individual coordinate $X_1, Y_1, X_2,$ or $Y_2$ in the example depicted in FIG. 9 depends in fact on the previous choice of the pair of angles $\alpha$ and $\beta$, which determine the specific shape of the triangle. In addition, only discrete values would be allowed for any given coordinate to avoid any confusion between identification codes that differ only by the value of a single coordinate. In practice, the incremental step between two consecutive values allowed for a spatial coordinate is dictated by the overall resolution of the optical reading scheme. This resolution depends on factors such as the intrinsic size of each inscribed mark, the lateral resolution (or resolving power) of the microscope objective 162 of the optical reader 28, the dimensions of the sensitive photoelements of the array sensor of the CCD camera 166, and the ability to get an image of the marks in sharp focus. For example, it could be safe to specify an incremental step of about 4 µm for the allowed spatial coordinates of marks having a diameter of 1 µm, to ensure that two neighbouring marks separated by the incremental step are always clearly distinguished in the images provided by the optical reader. This means that the X coordinate of the encoding marks could take a maximum of 75 different values if the triangle that delimits the indicium 198 would have a longest side of, let's say, L=300 µm. In the above example the number of allowed values for each coordinate will be in fact substantially lower than 75, since the two other sides of the triangle define the upper bounds of the intervals over which the coordinates can vary. This is particularly obvious for the coordinates $Y_1$ and $Y_2$ related to the vertical positions of the encoding marks 202A and 202B in FIG. 9.

Figure 10A:
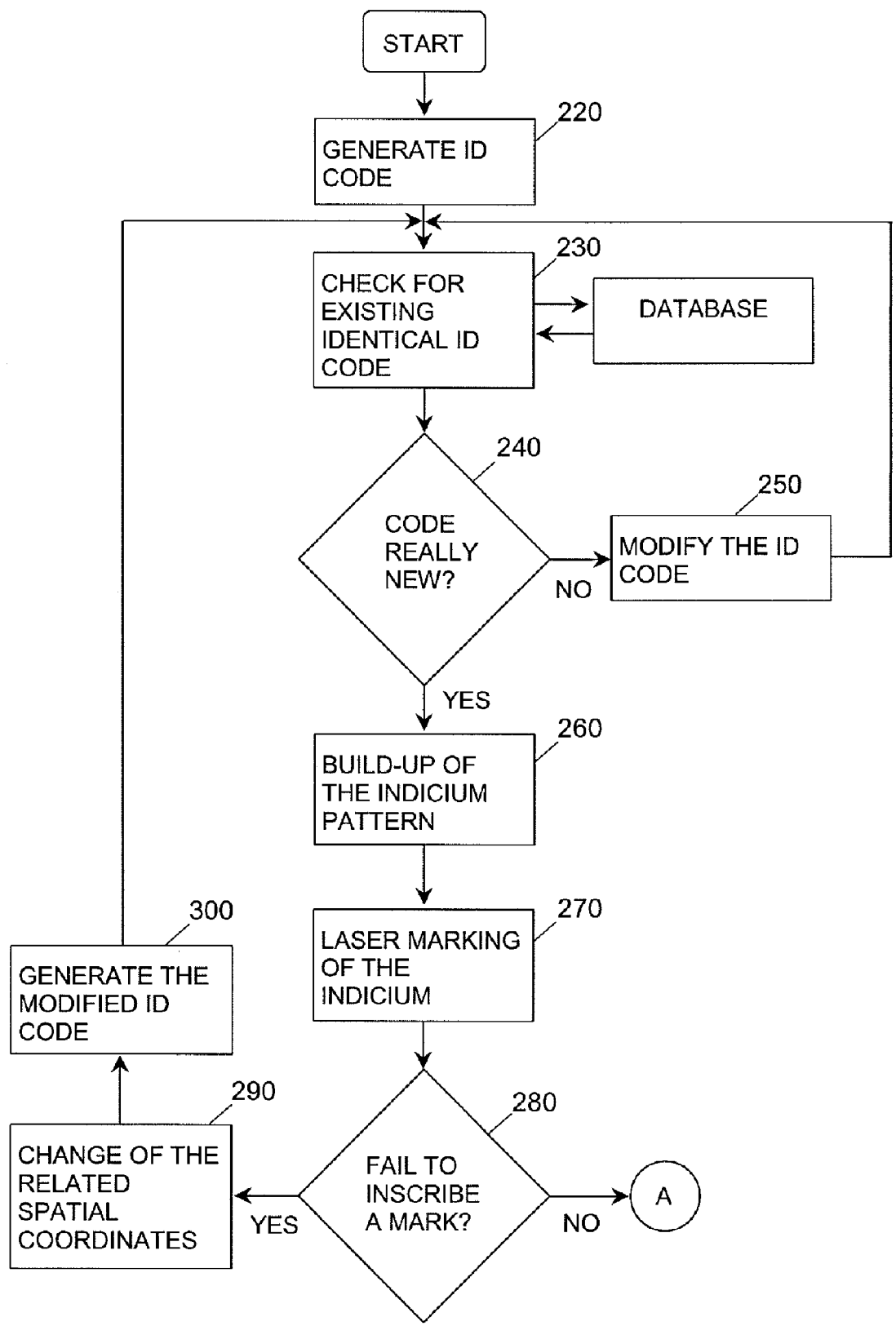
FIGS. 10A and 10B illustrate a flow chart of the sequence of operations performed by the gemstone authentication system to inscribe an indicium in the volume of a gemstone according to the method of the present invention.
Figure 10B:
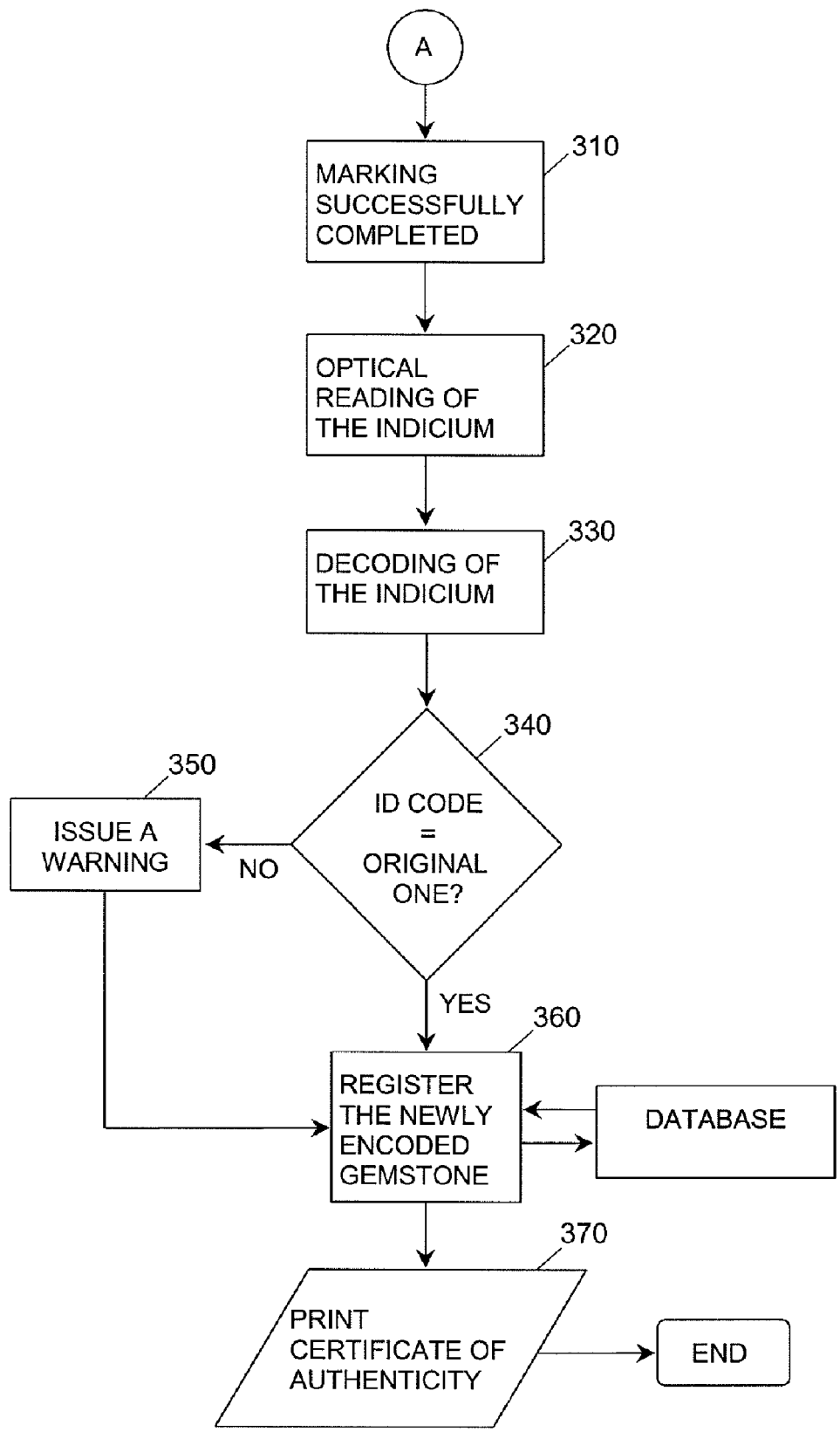

Procedure for Laser Marking in Gemstones by Benefiting from the Presence of Internal Defects and Impurities A preferred sequence of operations for laser inscription of indicia in the volume of gemstone is depicted in the flow chart diagram presented in FIGS. 10A and 10B. This sequence is performed via communications between the CPU 20 of the gemstone authentication system depicted in FIG. 2 and a remote laser marking station 26. In a first step 220, the CPU 20 generates an identification code (labelled ID code in FIGS. 10A and 10B) in accordance with the requirements and rules specified in the encoding scheme implemented in the authentication system. The CPU 20 then accesses to the database 22 in step 230 to check if the newly generated ID code would have been already attributed to a previously marked gemstone. If the ID code is found to be a reserved one in step 240, it is then immediately modified 250, and a further check 230 is performed until a valid ID code is finally obtained. From the selected ID code, the corresponding pattern of the indicium is then generated in step 260, according to a preferred symbology such as the one depicted in FIG. 9. The build-up of the pattern for the indicium consists basically in establishing the relative spatial position of each of the various marks that will form part of the indicium, so that the ID code becomes faithfully encrypted in the pattern. The pattern of the indicium is then converted to a sequence of machine instructions that is transmitted to the laser marking station 26 to enable the marking process in step 270. The marks are engraved in sequential order and the gemstone is kept immobile as the inscription of each individual mark proceeds. After successful completion of the marking run for any given mark, the motorized translation stages 124A, 124B and 124C of the workpiece mount assembly 54 (see FIG. 4) move the gemstone 120 until the next marking location coincides precisely with the optical axis of the write laser beam.

A novel aspect of the present invention is that the laser-induced structural changes in the diamond material that lead to the growth of an opaque mark are initiated by defects or impurities present within the volume in the material where the write laser beam gets its smaller transverse size or, equivalently, its maximum optical fluence. Natural diamonds typically contain a variety of invisible structural defects and impurities, most of them being impurity atoms such as nitrogen, hydrogen and boron, the most common of these being nitrogen. Initiating the marking of dot-shaped structures from internal defects allows the marking process to begin with femtosecond laser pulses carrying an energy well below the threshold energy required for creating structural changes in an otherwise perfect diamond material. As a consequence, the write laser beam can be emitted from Ti:Sapphire laser oscillators, without having to provide any subsequent optical amplification of the laser pulses. In addition, the risks of inflicting optical damages to the table of the gemstone are dramatically reduced by using laser pulses having "safe" optical fluence levels in a plane that coincides with the table.

Figure 1A:
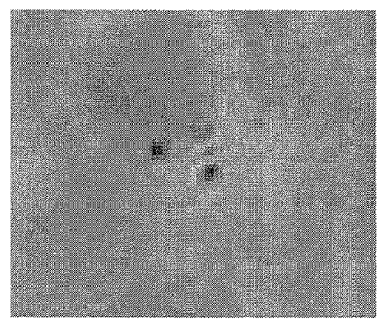
FIGS. 1A, 1B and 1C are optical photomicrographs showing marks engraved in the bulk of various diamond samples.
Figure 1B:
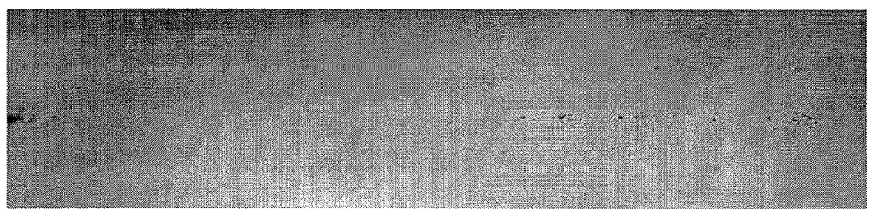
Figure 1C:
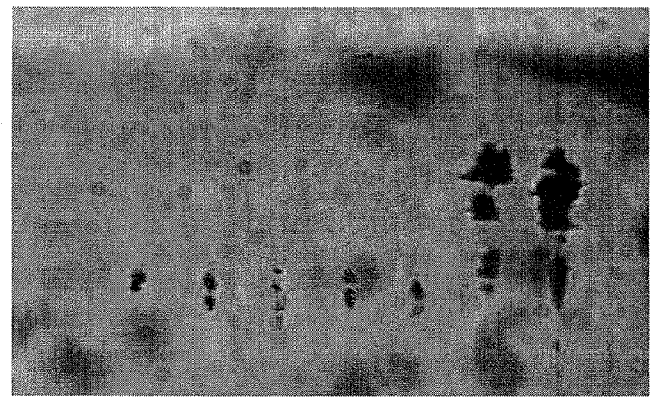

However, a major shortcoming in initiating the build-up of opaque marks from the naturally occurring defects and impurities originates from the random spatial distribution of these defects, along with their concentration that varies largely from site to site in the same gemstone. Furthermore, gemstones of very high quality, such as those graded as internally flawless, often have regions in their volume that are virtually free from any "useful" defect, thus requiring higher energy levels and/or a larger number of laser pulses. In practice, the protocol for laser marking would include a progressive increase of the energy per pulse until the growth of a mark is initiated. The maximum allowable energy would be determined by the specific laser system implemented in the marking station, and this energy could exceed the threshold energy for inducing structural changes in the bulk of a perfect gemstone material. As a result, the laser marking protocol would include the possibility of inscribing marks in a site that is free from any defect or impurities. However, as shown in FIGS. 1A and 1C, the probability of initiating the growth of undesired marks located everywhere along the path of the write laser beam inside of a gemstone increases when using higher energy levels. Nonlinear optical effects such as self-focusing may also limit the maximum energy per pulse allowed to inscribe in a reliable and safe way in gemstones such as diamonds, particularly when using a focusing objective of lower numerical aperture.

The method of the present invention gets rid of the random distribution of the internal defects and impurities in a gemstone to be marked by performing a real-time monitoring of the growth of each individual mark. In case of failure in inscribing any given mark in step 280, due presumably to the absence of defects in the volume around the focused write laser beam, the CPU 20 is informed of the failure event and a new engraving position for the mark is determined, as indicated in step 290 of FIG. 10A. An ID code modified according to the newly determined position of the mark is calculated in step 300, and its validity is then confirmed through steps 230-240. The laser marking 270 at the new location is then started. The procedure is repeated until the mark can be successfully inscribed, and the overall method is applied to the whole set of marks that form the indicium. As a result, the ID code and its related indicium obtained at the end 310 of a successful marking run can differ appreciably from those generated at the very beginning of the marking run, particularly when engraving in gemstones having a very high clarity.

Figure 11:
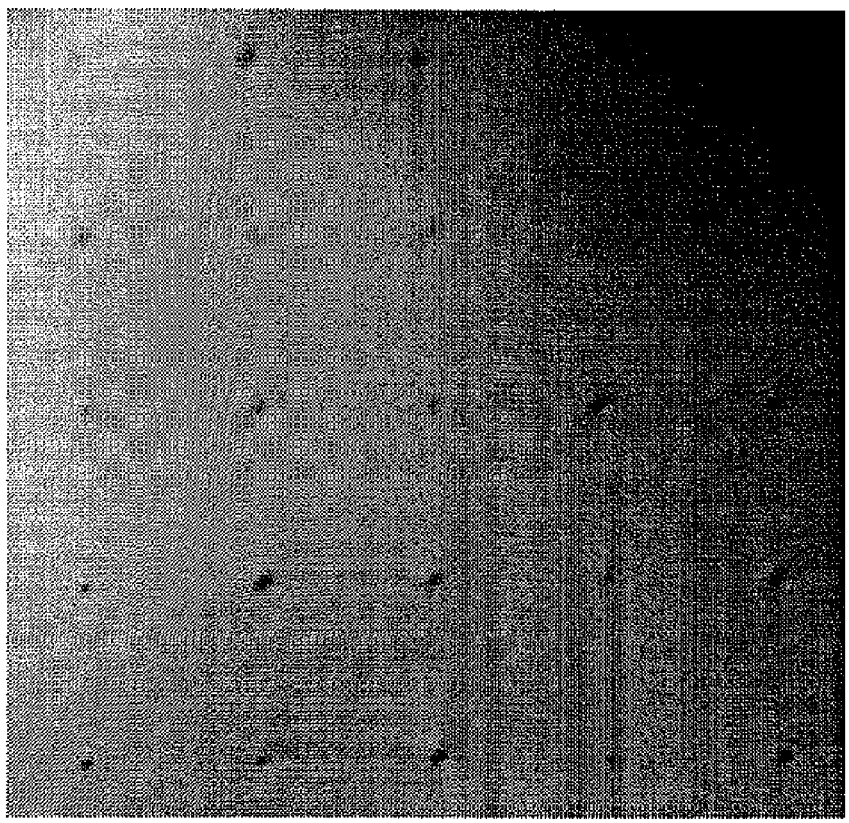
FIG. 11 is an optical photomicrograph showing an array of 25 dot-shaped marks engraved in the volume of a natural diamond sample.

FIG. 11 shows an optical photomicrograph of a 5×5 square array of dot-shaped marks that have been inscribed in a controlled manner at a depth of about 300 µm below the table of a natural diamond gemstone, according to an exemplary laser marking protocol. The selected protocol consisted in delivering on the gemstone a first pair of laser pulses having a wavelength of 775 nm and a pulse duration of about 150 fs as measured right at the output of the laser system. Both laser pulses were separated from each other by a time interval of 1 ms. The laser pulses have been focused with an objective made from a single aspheric lens having a numerical aperture of 0.5 for a transverse beam intensity distribution of about 8-mm diameter at its entrance pupil. The energy per pulse of the write laser beam as measured at the entrance pupil of the focusing objective was slightly less than 1 µJ. Successive pairs of laser pulses with characteristics identical to those given above were directed onto the sites until the final diameter of each mark was in the range of about 3 to 5 µm. As its marking proceeded, each site was imaged onto a CCD camera to monitor the progressive growth of the mark. A mark of suitable diameter could be inscribed at each of the 25 distinct sites in this specific diamond sample, without any failure. The number of pulse pairs required to inscribe a mark with suitable diameter was variable from site to site, but it never exceeded five for the specified energy per pulse. The depth at which the marks have been inscribed showed some variation from site to site, so that it was not possible to bring the images of all of the marks in sharp focus in the same photomicrograph. The spacing between neighbouring marks shown in FIG. 11 is about 50 µm. The array of dot-shaped marks covers an area of about 250 µm×250 µm, which corresponds to the typical overall size of an indicium engraved according to the method of the present invention.

Returning back to FIG. 10B, in step 320 an optical reader 28 that forms part of the equipment of the laser marking station 26 provides a machine-readable image of the indicium newly engraved in the gemstone. The CPU 20 retrieves the ID code from the image of the indicium in step 330, and this ID code is then compared 340 with the ID code that was currently valid at the end of the marking run. In theory, both ID codes should be identical, but potential failures or defective operation of the hardware of the laser marking station 26 may lead to differences between the desired ID code and the one that corresponds to the indicium actually engraved in the gemstone 120. The CPU 20 issues a warning to the operator of the laser marking station in step 350 if this event occurs. The newly-engraved gemstone is then registered 360 in the authentication system by recording in the database 22 the ID code as retrieved in step 330 along with some other identification data. The data package recorded in the database can include the specific image captured by the optical reader 28 and that was processed by the CPU 20 to retrieve the ID code of the gemstone. Finally, a certificate of authenticity is printed in step 370 to complete the sequence of operations.

While the preferred embodiment of the invention in its various aspects has been described above, such description is to be taken as illustrative of an embodiment of the invention rather than description of the intended scope of the invention, which scope will be more fully appreciated by reference to the disclosure as a whole.

What is claimed is:

1. A method for adaptive control of the creation of indicia in the bulk of a gemstone specimen using a series of laser pulses in the femtosecond range focused below the surface of said specimen, said mdicia identifying said specimen without affecting the surface of the specimen and being invisible under 10× magnification, comprising:
predetermining characterizing features of the indicia to be created;
executing a predetermined marking protocol for said series of laser pulses using parameters selected from among the group comprising wavelength, pulse duration, number of pulses, repetition rate, energy per pulse, numerical aperture of focusing optics and target coordinates;
automatically monitoring the creation of said indicia as said protocol is being executed; and,
automatically interrupting further execution of said protocol when said monitoring reveals that said indicia exhibits said characterizing features.

2. The method of claim 1 wherein said characterizing features are selected from the group comprising shape, size, optical properties and location in the specimen.

3. The method of claim 2 wherein said characterizing features comprises size and said size is a size that does not decrease the commercial value of said specimen.

4. The method of claim 2 wherein said step of monitoring comprises monitoring the creation of said indicia as said protocol is being executed and varying at least one of said parameters based on the result of said monitoring.

5. The method of claim 1 wherein said marking protocol comprises a plurality of sets of said parameters for sequential execution of said sets.

6. The method of claim 5 wherein each successive set comprises a change in the energy per pulse over the preceding set in the sequence.

7. The method of claim 1 wherein said monitoring is conducted using an imaging optical set-up to assess the presence of said characterizing features.

8. The method of claim 7 further comprising the use of a fast photodetector to detect pulses of light signaling structural changes in said specimen and an optical filter.

9. The method of claim 1, 5, 6, 7 or 8 wherein said gemstone specimen is diamond.

10. An adaptive control method for controlling the creation of indicia in the bulk of a gemstone specimen, said indicia identifying said specimen without affecting the surface of the specimen and being invisible under 10× magnification, using a series of laser pulses in the femtosecond range and focused below the surface of said specimen, comprising:
predetermining characterizing features of the indicia to be created;
under control of a processing unit, generating an identification code for association with said specimen;
determining a characteristic pattern for a plurality of indicia corresponding to said identification code;
executing a predetermined marking protocol for said series of laser pulses to attempt to sequentially create each of said indicia according to said characteristic pattern, using parameters selected from among the group comprising wavelength, pulse duration, number of pulses, repetition rate, energy per pulse, numerical aperture of focusing optics and target coordinates;
automatically monitoring the creation of said indicia as said protocol is being executed; controlling said processing unit such that if execution of said protocol creates one but not all of said mdicia according to said characteristic pattern, said processing unit causes the generation of a new identification code corresponding to a new characteristic pattern that is consistent with those of said indicia that have been successfully created, and if required said processing unit causes execution of a marking protocol to create additional indicia to attempt to complete said new characteristic pattern;
automatically interrupting further execution of said protocol when said indicia exhibits said characterizing features; and, upon completing the creation of said characteristic pattern of indicia or said new characteristic pattern of indicia, recording said identification code or said new identification code, as the case may be, in a database.

11. The method of claim 10 wherein said gemstone specimen is diamond.

12. An adaptive control method for controlling the application of indicia in the bulk of a gemstone specimen using a series of laser pulses in the femtosecond range focused below the surface of said specimen, said indicia identifying said specimen without affecting the surface of the specimen and being invisible under 10× magnification, comprising:
under control of a processing unit, generating an identification code for association with said specimen;
determining a characteristic pattern for a plurality of indicia corresponding to said identification code;
under control of said processing unit, executing a marking protocol for said series of laser pulses by applying said pulses to attempt to sequentially create each of said indicia according to said characteristic pattern; and,
controlling said processing unit such that if execution of said protocol creates one but not all of said indicia according to said characteristic pattern, said processing unit causes the generation of a new identification code corresponding to a new characteristic pattern that is consistent with those of said indicia that have been successfully created, and if required said processing unit executes a marking protocol to create additional indicia to attempt to complete said new characteristic pattern.

13. The method of claim 12 further comprising the step of monitoring the creation of each of said plurality of indicia in turn.

14. The method of claim 12 further comprising the step of, upon completing the creation of said characteristic pattern of indicia or said new characteristic pattern of indicia, recording said identification code or said new identification code, as the case may be, in a database.

15. The method of claim 14 wherein said step of generating an identification code further includes the step of ascertaining from said database whether said identification code is available and if not, generating a further identification code and ascertaining from said database whether said further identification code is available.

16. The method of claims 12, 13, 14 or 15 wherein said gemstone specimen is diamond.

17. A gemstone authenticating system comprising:
marking apparatus for applying patterns of indicia in the bulk of gemstones using a series of ultrashort laser pulses focused below the surface of gemstones, said indicia being invisible under 10× magnification, said marking apparatus further comprises an imaging optical set-up for assessing the creation of indicia in real time;
a database uniquely associating an identification code with each of said patterns of indicia;
a plurality of reading apparatus associated with a plurality of remote locations for detecting said patterns of indicia; and,
a processing unit configured to communicate with said marking apparatus, said database and said reading apparatus, said processing unit being configured to:
control the operation of said marking apparatus according to the status of creation of indicia;
to adapt parameters for said series of laser pulses according to an assessment of the creation of indicia in real time; and,
to communicate to said database the successful application of a pattern of indicia.

18. The system of claim 17 wherein said processing unit is configured to select an alternate pattern of indicia in the event that a predetermined pattern of indicia is not successfully applied to said gemstones.

19. The system of claim 18 wherein said processing unit is configured to consult said database in selecting said alternate pattern of indicia.

20. An adaptive control method for controlling the creation of indicia in the bulk of a gemstone specimen, said indicia identifying said specimen without affecting the surface of said specimen and being invisible under 10× magnification, comprising:
establishing a marking protocol for an ultrashort laser pulse marking system, said protocol comprising a plurality of predetermined sets of parameters, each set comprising parameters selected from among the group comprising wavelength, pulse duration, number of pulses, repetition rate, energy per pulse, numerical aperture of focusing optics, and target coordinates;
attempting to create an indicium by executing a first set of parameters determined by said protocol;
automatically assessing whether an indicium was created using said first set of parameters;
if an indicium was not created, automatically attempting to create an indicium according to a second set of parameters determined by said protocol.

21. The method of claim 20 wherein said gemstone specimen is diamond.

22. A diamond specimen comprising at least three sub-surface indicia artificially inscribed therein for identifying said specimen, and wherein said at least three indicia are coded as a spatial arrangement of localized areas wherein each of said localized areas exhibits optical characteristics that are different from those surrounding said localized area, each of said indicia being invisible under 10× magnification, being 3 µm or less in any dimension and being located at a depth of at least 200 µm below the surface of said specimen.

23. The specimen of claim 22 wherein a first subset of said plurality defines a coordinate system and a second subset of said plurality encodes identification data relating to said specimen.

24. A method for adaptive control of the creation of indicia in the bulk of a gemstone specimen using a series of laser pulses in the femtosecond range focussed below the surface of said specimen, said indicia identifying said specimen without affecting the surface of the specimen and being invisible under 10× magnification, comprising:
predetermining characterizing features of the indicia to be created;
undertaking the execution of a predetermined marking sequence of said laser pulses using parameters selected from among the group comprising wavelength, pulse duration, number of pulses, repetition rate, energy per pulse and numerical aperture of focusing optics;
monitoring the creation of said indicia as said sequence is being executed; and,
immediately interrupting the continued execution of said sequence when said monitoring reveals that said indicia exhibits said characterizing features.

25. The method of claim 24 wherein said characterizing features are dimensional features.

26. The method of claim 25 wherein said gemstone is diamond.

27. Apparatus for applying indicia in the bulk of gemstones, said indicia identifying said gemstones and being invisible under 10 × magnification, comprising:
- a laser system for focussing laser pulses of less than 100 femtoseconds at selected depths below the surface of a gemstone;
- memory means containing a marking protocol comprising parameters for the operation of said laser system, said parameters being predetermined and selected from among the group comprising pulse duration, number of pulses, repetition rate, energy per pulse and numerical aperture;
- a CPU for controlling the operation of said laser system according to said marking protocol; and,
- an automatic process monitoring unit for assessing the creation of each indicium after each pulse.

28. The apparatus of claim 27 wherein said CPU controls the operation of said laser system according to the process monitoring unit's assessment of the creation of said indicium.

29. The apparatus of claim 28 wherein said protocol comprises a plurality of sets of said parameters for sequential execution, and said CPU acts to cause a second set of said parameters to be executed if a first set of parameters fails to cause the creation of an indicium.

30. The apparatus of claim 29 wherein said second set comprises different energy per pulse than said first set.

31. The apparatus of claim 27 or 30 wherein said process monitoring unit comprises an imaging optical set-up.

32. The apparatus of claim 27 or 30 wherein said process monitoring unit comprises an optical filter in conjunction with a fast photodetector.

33. The apparatus of claim 27 or 30 further comprising a write beam diagnostic sub-system comprising at least one optical channel selected from a among the group comprising an image capture means, a pulse counter and an optical power meter.

34. The apparatus of claim 27 further comprising a database for uniquely associating data for each of a plurality of gemstones with patterns of indicia recorded in said gemstones, and wherein said CPU causes execution of said marking protocol upon target coordinates determined by one of said patterns of indicia.

35. The apparatus of claim 29 further comprising a database for uniquely associating data for each of a plurality of gemstones with patterns of indicia recorded in said gemstones, and wherein said CPU is configured to attempt to execute said marking protocol upon target coordinates determined by one of said patterns of indicia, and if one indicium of said pattern is not created upon execution of said protocol, to communicate with said database to retrieve an alternate pattern of indicia.

36. The apparatus of claim 27, 28, 29 or 30 wherein said gemstone is diamond.

37. The apparatus of claim 28 wherein said CPU acts to vary the parameters according to which said operation is controlled according to the process monitoring unit's assessment of the creation of said indicia.

* * * * *